US 7,968,752 B2

(12) United States Patent
Lee et al.

(10) Patent No.: US 7,968,752 B2
(45) Date of Patent: *Jun. 28, 2011

(54) HYDROLYTICALLY-RESISTANT BORON-CONTAINING THERAPEUTICS AND METHODS OF USE

(75) Inventors: Ving Lee, Los Altos, CA (US); Jacob J. Plattner, Berkeley, CA (US); Stephen J. Benkovic, State College, PA (US); Stephen J. Baker, Mountain View, CA (US); Kirk R. Maples, San Jose, CA (US); Carolyn Bellinger-Kawahara, Redwood City, CA (US); Tsutomu Akama, Sunnyvale, CA (US); Yong-Kang Zhang, San Jose, CA (US); Rajeshwar Singh, Edmonton (CA); Vittorio A. Sauro, Edmonton (CA)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/270,636

(22) Filed: Nov. 13, 2008

(65) Prior Publication Data
US 2009/0239824 A1    Sep. 24, 2009

Related U.S. Application Data

(63) Continuation of application No. 10/868,268, filed on Jun. 15, 2004, now Pat. No. 7,465,836.

(60) Provisional application No. 60/478,921, filed on Jun. 16, 2003.

(51) Int. Cl.
 *C07F 9/02* (2006.01)
(52) U.S. Cl. .............................................. 568/8
(58) Field of Classification Search .................. None
See application file for complete search history.

(56) References Cited

U.S. PATENT DOCUMENTS 5,880,188 A *   3/1999 Austin et al. ............ 524/109
7,465,836 B2 * 12/2008 Lee et al. ........................ 568/8

FOREIGN PATENT DOCUMENTS

CA          2225014       6/1999
WO      WO 03033002       4/2003

OTHER PUBLICATIONS

Genaev, A., et al., "Intramolecular Borylation Reaction Catalyzed by Lewis Acid: Preparation of 1H-2,1-Benzazaborole Derivatives", Chemical Communications, 2000, vol. 17; pp. 1587-1588.

* cited by examiner

*Primary Examiner* — Daniel M Sullivan
*Assistant Examiner* — Yevegeny Valenrod
(74) *Attorney, Agent, or Firm* — Morgan, Lewis & Bockius, LLP

(57) ABSTRACT

Compositions and methods of use of borole derivatives, including benzoxaboroles, benzazaboroles and benzthiaboroles, as therapeutic agents for treatment of diseases caused by bacteria or viruses are disclosed, as well as methods for synthesis of said agents and compositions thereof.

48 Claims, No Drawings

HYDROLYTICALLY-RESISTANT BORON-CONTAINING THERAPEUTICS AND METHODS OF USE

This application is a continuation of U.S. patent application Ser. No. 10/868,268 filed Jun. 15, 2004, now U.S. Pat. No. 7,465,836, which claims priority of U.S. Provisional Application Ser. No. 60/478,921, filed Jun. 16, 2003, the full disclosure of which is incorporated herein by reference for all purposes.

FIELD OF THE INVENTION

The present invention relates to novel compounds and compositions which have selective therapeutic activities, processes for making such compounds, synthetic intermediates employed in these processes and a method for treating human or other mammal in need of medical treatments.

BACKGROUND OF THE INVENTION

Many advances in medicine in the $20^{th}$ century have been due to the discovery of new classes of small molecular weight effectors for various therapeutic needs. Herein we disclose the diverse, but selective pharmacologically active boron-containing entities.

One hallmark of the modern era of medicine has been the decline in morbidity and mortality associated with bacterial and fungal infections. However, misuse of conventional antibiotics and natural selection of the infectious bacterial population has resulted in the development of varying degrees of drug resistance by most bacterial infectious agents to most antibiotic agents. In severe cases, such as MRSA (Multidrug-Resistant StaphA), one or only a few antibiotics are currently effective. In addition, the existence of immunodeficiency syndromes results in additional incidences of opportunistic infections requiring intensive antibiotic treatment.

Viruses are implicated in a variety of animal and human disease. Numerous approaches have been proposed to combat these pathogens which include, but are not limited to herpesviruses 1 and 2 (HSV-1 and HSV-2), influenza viruses A, B and C, parainfluenza viruses 1-4, syncytial virus, Epstein-Barr virus, rhinoviruses, human immunodeficiency viruses (HIV), polioviruses, coxsackieviruses, echoviruses, rubella virus, varicella-zoster virus, neuroderma-tropic virus, variola virus, cytomegalovirus, hepatitis A, B and C viruses, papoviruses, rabies virus, yellow fever virus, dengue virus, West Nile virus and SARS virus.

One approach in the development of antiviral compounds has been to identify compounds which interfere with the normal viral metabolism and replication in infected host cells. During the screening of new borinic ester compounds, we have found that certain of these compounds show antiviral activity in cell culture assay systems. Many existing compounds currently in use for treating viral diseases are subject to resistance mechanisms, are expensive to make, do not adequately treat patients or have adverse side effects. Therefore, there is a continuing need for new compounds which act to kill viruses, to inhibit viral replication or to block the pathogenic action of viruses.

| Virus Category | Pertinent Human Infections |
| --- | --- |
| RNA Viruses | |
| Picomaviridae | Polio |
| | Human hepatitis A |
| | Human rhinovirus |
| Togaviridae and Flaviviridae | Rubella - German measles |
| | Yellow fever |
| Coronaviridae | Human respiratory coronavirus (HCV) |
| | Severe acute respiratory syndrome (SAR) |
| Rhabdoviridae | Lyssavirus - Rabies |
| Paramyxoviridae | Paramyxovirus - Mumps |
| | Morbillvirus - measles |
| | Pneumovirus - respiratory syncytial virus |
| Orthomyxoviridae | Influenza A-C |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovirus - Sandfly fever (SFN) |
| | Uukuvirus - Uukuniemi (UUK) |
| | Rift Valley Fever (RVFN) |
| Arenaviridae | Junin - Argentine hemorrhagic fever |
| | Machupo - Bolivian hemorrhagic fever |
| | Lassa - Lassa fever |
| | LCM - aseptic lymphocyctic choriomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| DNA Viruses | |
| Papovaviridae | Pediatric viruses that reside in kidney |
| Adenoviridae | Human respiratory distress and some deep-seated eye infections |
| Parvoviridae | Human gastro-intestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Varicella zoster virus (VZV) |
| | Epstein-Barr virus (EBV) |
| | Human herpes virus 6 (HHV6) |
| Poxviridae | Orthopoxvirus is sub-genus for smallpox |
| Hepadnaviridae | Hepatitis B virus (HBV) |
| | Hepatitis C virus (HCV) |

Boron containing compounds have received increasing attention as therapeutic agents over the past few years as technology in organic synthesis has expanded to include this atom. [Boron Therapeutics on the horizon, Groziak, M. P.; American Journal of Therapeutics (2001) 8, 321-328] The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides [Organic boron compounds as herbicides. Barnsley, G. E.; Eaton, J. K.; Airs, R. S.; (1957), DE 1016978 19571003], boron neutron capture therapy [Molecular Design and Synthesis of B-10 Carriers for Neutron Capture Therapy. Yamamoto, Y.; Pure Appl. Chem., (1991) 63, 423-426], serine protease inhibition [Borinic acid inhibitors as probes of the factors involved in binding at the active sites of subtilisin Carlsberg and α-chymotrypsin. Simpelkamp, J.; Jones, J. B.; Bioorganic & Medicinal Chemistry Letters, (1992), 2(11), 1391-4], [Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307], acetylcholinesterase inhibition [New, specific and reversible bifunctional alkylborinic acid inhibitor of acetylcholinesterase. Koehler, K. A.; Hess, G. P.; Biochemistry (1974), 13, 5345-50] and as antibacterial agents [Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553]. The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity [Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184]. Synthetic developments described in Benkovic et al. enabled creation of a much more diverse class of unsymmetrical di-substituted borinic acid complexes not possible before.

Thus, there continues to be a need in the medical arts for novel, more effective, antibiotic compounds, especially for treating infectious diseases, that are resistant to currently available therapies.

BRIEF SUMMARY OF THE INVENTION

In one aspect, the present invention relates to therapeutic compounds, which are boron-containing. These compounds include structures that encompass benzoxaboroles, benzazaboroles, benzthiaboroles and related analogs.

These compounds are also provided as pharmaceutical compositions that can be administered to an animal, most preferably a human, for treatment of a disease having either bacterial, fungal or viral etiology, most preferably a human, in an immunologically compromised or debilitated state of health.

In preferred embodiments, the compounds of the invention are those having the structures given by Formula 1, with preferred substituents as disclosed herein.

The invention also provides methods for preparing these therapeutic compounds and pharmaceutical compositions thereof, and methods of using said compounds therapeutically. Kits and packaged embodiments of these compounds and pharmaceutical compositions of the invention are also contemplated.

The invention also relates to methods of treating various medical conditions, using the compounds disclosed herein.

DETAILED DESCRIPTION OF THE INVENTION

This invention provides therapeutic agents, and specifically antibacterial, antifungal, or antiviral compounds, useful in treating and/or preventing conditions due to these pathogens.

The invention comprises a compound having the following structures

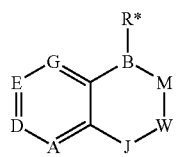

Formula 1 wherein B is boron, M is selected from oxygen, sulfur and NR**, wherein R* is selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted aryl, and substituted or unsubstituted heteroaryl, wherein R** is H, alkyl, alkyloxy, alkoxyalkyl, substituted or unsubstituted aryl, substituted or unsubstituted heteroaryl, and wherein A is CH, $CR^1$, or N and wherein D is CH, $CR^2$, or N and wherein E is CH, $CR^3$, or N and wherein G is CH, $CR^4$, or N and the combination of nitrogens (A+D+E+G) is 0-3 and wherein J is $(CH_2)_n$ (n=0 to 2) or $CHR^5$ and wherein W is $(CH_2)_m$ (m=0 to 1), C=O (carbonyl) or $CHR^6$ wherein $R^1$, $R^2$, $R^3$ and $R^4$ are each independently selected from the group consisting of hydrogen, haloalkyl, alkyl, cycloalkyl, $(CH_2)_p$OH (p=1 to 3), halogen, CHO, CH=NOH, $CO_2H$, $CO_2$-alkyl, S-alkyl, $SO_2$-alkyl, S-aryl, $(CH_2)_q NR^{18} R^{19}$ (wherein $R^{18}$ and $R^{19}$ are independently selected from hydrogen, alkyl, and alkanoyl)(q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl, wherein $R^5$ is selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted aryl, and substituted or unsubstituted heteroaryl, wherein $R^6$ is selected from substituted or unsubstituted alkyl ($C_1$-$C_4$), substituted or unsubstituted cycloalkyl ($C_3$-$C_7$), substituted or unsubstituted alkenyl, substituted or unsubstituted alkynyl, substituted or unsubstituted aralkyl, substituted or unsubstituted aryl, and substituted or unsubstituted heteroaryl, including salts thereof, especially all pharmaceutically acceptable salts.

In preferred embodiments of Formula 1, M is oxygen, or M is sulfur, or M is NR**. Further preferred embodiments of any of these three are any of the following.

In a preferred embodiment of Formula 1, R* is a substituted or unsubstituted alkyl ($C_1$-$C_4$).

In a preferred embodiment of Formula 1, R* is a substituted or unsubstituted cycloalkyl ($C_3$-$C_7$).

In a preferred embodiment of Formula 1, R* is a substituted or unsubstituted alkenyl. In a further preferred embodiment thereof, the substituted alkenyl has the structure

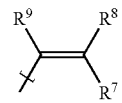

wherein $R^7$, $R^8$, and $R^9$ are each independently selected from the group consisting of hydrogen, alkyl, haloalkyl, aryl, substituted aryl, aralkyl, substituted aralkyl, $(CH_2)_r$OH (where r=1 to 3), $CH_2NR^{20}R^{21}$ (wherein $R^{20}$ and $R^{21}$ are independently selected from hydrogen and alkyl), $CO_2H$, $CO_2$alkyl, $CONH_2$, S-alkyl, S-aryl, $SO_2$alkyl, $SO_3H$, $SCF_3$, CN, halogen, $CF_3$ and $NO_2$.

In a preferred embodiment of Formula 1, R* is a substituted or unsubstituted alkynyl. In a further preferred embodiment thereof the substituted alkynyl has the structure

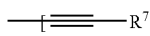

wherein $R^7$ is defined as before.

In a preferred embodiment of Formula 1, R* is a substituted or unsubstituted aryl. In a further preferred embodiment thereof the substituted aryl has the structure

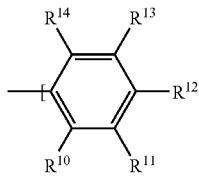

Wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s OH$ (where s=1 to 3), $CO_2H$, $CO_2$alkyl, $CONH_2$, $CONH$alkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_t NR^{22}R^{23}$ (wherein $R^{20}$ and $R^{21}$ are independently selected from hydrogen, alkyl, and alkanoyl) (t=0 to 2), $SO_2NH_2$, $OCH_2CH_2NH_2$, $OCH_2CH_2NH$alkyl, $OCH_2CH_2N(alkyl)_2$, oxazolidin-2-yl, or alkyl substituted oxazolidin-2-yl.

In a preferred embodiment of Formula 1, R* is a substituted or unsubstituted aralkyl. In a further preferred embodiment thereof the substituted aralkyl has the structure

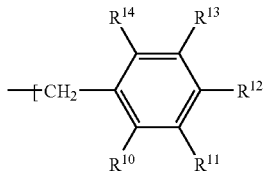

wherein $R^{10}$, $R^{11}$, $R^{12}$, $R^{13}$ and $R^{14}$ are defined as before.

In a preferred embodiment of Formula 1, R* is a substituted or unsubstituted heteroaryl. In a further preferred embodiment thereof the heteroaryl has the structure

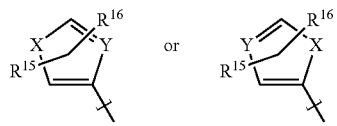

wherein X=CH=CH, N=CH, $NR^{17}$ (wherein $R^{17}$=H, alkyl, aryl or benzyl), O, or S
and wherein Y=CH or N
and wherein $R^{15}$ and $R^{16}$ are each independently selected from the group consisting of hydrogen, alkyl, cycloalkyl, haloalkyl, aryl, substituted aryl, aralkyl, substituted aralkyl, $(CH_2)_u OH$ (where u=1, 2 or 3), $(CH_2)_v NR^{24}R^{25}$ (wherein $R^{24}$ and $R^{25}$ are independently selected from hydrogen, alkyl and alkanoyl) (v=0 to 3), $CO_2H$, $CO_2$alkyl, $CONH_2$, S-alkyl, S-aryl, $SO_2$alkyl, $SO_3H$, $SCF_3$, CN, halogen, $CF_3$ and $NO_2$.

The structures of the invention also permit solvent interactions that may afford structures (Formula 1B) that include atoms derived from the solvent encountered by the compounds of the invention during synthetic manipulations and therapeutic uses. Structures 1B arise from formation of a dative bond between the solvent(s) with the Lewis acidic boron center. Thus, such solvent complexes 1B could be stable entities with comparative bioactivities. Such structures are expressly contemplated by the present invention where R*** is H or alkyl.

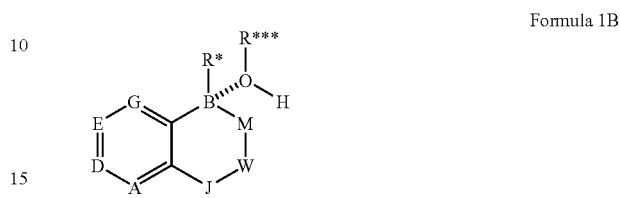

Formula 1B

As used herein, the following terms have the stated meaning:

By "alkyl", "lower alkyl", and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkanoyl" in the present invention is meant straight or branched chain alkanoyl groups having 1-6 carbon atoms, such as, acetyl, propanoyl, butanoyl, pentanoyl, hexanoyl, isobutanoyl, 3-methylbutanoyl, and 4-methylpentanoyl.

By "alkoxy", "lower alkoxy", and "$C_1$-$C_6$ alkoxy" in the present invention is meant straight or branched chain alkoxy groups having 1-6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By "cycloalkyl", e.g., $C_3$-$C_7$ cycloalkyl, in the present invention is meant cycloalkyl groups having 3-7 atoms such as, for example cyclopropyl, cyclobutyl, cyclopentyl, cyclohexyl, and cycloheptyl. In the $C_3$-$C_7$ cycloalkyl groups, preferably in the $C_5$-$C_7$ cycloalkyl groups, one or two of the carbon atoms forming the ring can optionally be replaced with a hetero atom, such as sulfur, oxygen or nitrogen. Examples of such groups are piperidinyl, piperazinyl, morpholinyl, pyrrolidinyl, imidazolidinyl, oxazolidinyl, perhydroazepinyl, perhydrooxazapinyl, oxepanyl, perhydrooxepanyl, tetrahydrofuranyl, and tetrahydropyranyl. $C_3$ and $C_4$ cycloalkyl groups having a member replaced by nitrogen or oxygen include aziridinyl, azetidinyl, oxetanyl, and oxiranyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred aryl groups include phenyl and naphthyl, each of which is optionally substituted as defined herein.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, and benzoxazolyl. Preferred heteroaryls are thiazolyl, pyrimidinyl, preferably pyrimidin-2-yl, and pyridyl. Other preferred heteroaryl groups include 1-imidazolyl, 2-thienyl, 1-(or 2-)quinolinyl, 1-(or 2-)isoquinolinyl, 1-(or 2-)tetrahydroisoquinolinyl, and 2-(or 3-)furanyl.

The invention also provides embodiments of the compounds disclosed herein as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, hydroxyethanesulfonic, nitric, benzoic, citric, tartaric, maleic, hydroiodic, alkanoic such as acetic, $HOOC-(CH_2)_n-CH_3$ where n is 0-4, and the like. Non-toxic pharmaceutical base addition salts include salts of bases such as sodium, potassium, calcium, ammonium, and functional equivalents. Those skilled in the art will recognize a wide variety of non-toxic pharmaceutically acceptable addition salts.

For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler, can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethyl sulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC—(CH_2)_n—CH_3$ where n is 0-4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Preferred compounds of the invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat. B* 677: 1-27). Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al. 1975, in "The Pharmacological Basis of Therapeutics", Ch. 1, p. 1).

Dosage amount and interval can be adjusted individually to provide plasma levels of the active moiety that are sufficient to maintain bacterial cell growth inhibitory effects. Usual patient dosages for systemic administration range from 100-2000 mg/day. Stated in terms of patient body surface areas, usual dosages range from 50-910 mg/m²/day. Usual average plasma levels should be maintained within 0.1-1000 µM. In cases of local administration or selective uptake, the effective local concentration of the compound cannot be related to plasma concentration.

The compounds of the invention are useful as antibiotics for the treatment of diseases of both animals and humans, including but not limited to actinomycosis, anthrax, bacterial dysentery, botulism, brucellosis, cellulitis, cholera, conjunctivitis, cystitis, diphtheria, bacterial endocarditis, epiglottitis, gangerene, gastroenteritis, glanders, gonorrhea, Legionnaire's disease, leptospirosis, bacterial meningitis, plague, bacterial pneumonia, otitis media, puerperal sepsis, pyronephritis, rheumatic fever, Rocky Mountain spotted fever, scarlet fever, sinusitis, streptococcal pharyngitis, syphilis, tetanus, toxic shock syndrome, tuberculosis, tularemia, typhoid fever, typhus, and pertussis.

The compounds of the invention comprise a novel class of selective therapeutics. As antibacterial therapeutics, they inhibit medically-important bacterial species include gram-positive bacteria, including cocci such as *Staphylococcus* species and *Streptococcus* species; acid-fast bacterium, including *Mycobacterium* species; bacilli, including *Bacillus* species, *Corynebacterium* species, (*Propionibacterium* species and *Clostridium* species; filamentous bacteria, including *Actinomyces* species and *Streptomyces* species; gram-negative bacteria, including cocci such as *Neisseria* species and *Acinetobacter* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including Rickettsiae species and *Chlamydia* species.

Specific bacterial species that are targets for the antibiotics of the invention include *Propionibacterium acnes, Staphylococcus aureus; Staphylococcus epidermidis, Staphylococcus saprophyticus; Streptococcus pyogenes; Streptococcus agalactiae; Streptococcus pneumoniae; Enterococcus faecalis; Enterococcus faecium; Bacillus anthracia; Mycobacterium avium*-intracellulare, Mycobacterium tuberculosis, Acinetobacter baumannii; Corynebacterium diphtheria; Clostridium perfringens; Clostridium botulinum; Clostridium tetani; Neisseria gonorrhoeae; Neisseria meningitidis; Pseudomonas aeruginosa; Legionella pneumophila; Escherichia coli; Yersinia pestis; Haemophilus influenzae; Helicobacter pylori; Campylobacter fetus; Campylobacter jejuni, Vibrio cholerae; Vibrio parahcmolyticus parahaemolvticus; Trepomena pallidum; Actinomyces israelii; Rickettsia prowazekii; Rickettsia rickettsii; Chlamydia trachomatis; Chlamydia psittaci; Brucella abortus; Agrobacterium tumefaciens; and *Francisella tularensis*.

Medically-relevant fungal and yeast species that provide appropriate targets for the antifungal activity of the inhibitors of this invention include *Candida albicans, Candida glabrata, Candida krusei, Candida parapsilosis, Trichophyton mentagrophytes, Microsporium canis, Aspergillus* spp., *Cryptococcus neoformans, Blastomyces dermatitidis, Cocciodiodes immitis, Histoplasma capsulatum, Paracoccidiodes brasiliensis* and *Phycomycetes spp*.

The compounds of the invention are useful as antivirals for the treatment of diseases of both animals and humans, including but not limited to hepatitis A-C, yellow fever, respiratory syncytial virus, influenza, human immunodeficiency virus 1 and 2, adenoviruses, Norwalk virus, herpes simplex virus 1 and 2, cytomegalovirus (HCMV), varicella zoster, Epstein-Barr virus, and herpes viruses.

The disclosures in this application of all articles and references, including patents, are incorporated herein by reference.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

The compounds of this invention are evaluated for their antibacterial activity as per the guidelines and procedures prescribed by the National Committee for Clinical Laboratory Standards (NCCLS) (cf., NCCLS Document M7-A3, 1993—Antimicrobial Susceptibility Testing).

Protocol for MIC Determination

A useful protocol for MIC determination is as follows:
1. Approximately 2.5 mg of the compounds to be tested was weighed into cryovials.
2. 5 mg/ml stock solutions were made by adding DMSO to the samples accordingly.
3. 256 µg/ml working solutions were made by using the 5 mg/ml stock solutions and adding sterile distilled water accordingly.
4. A Beckman 2000 Automated Workstation was programmed to load 96 well plates with broth and compounds as follows:
   100 µl of the appropriate broth was added to columns 1-11
   200 µl of the appropriate broth was added to column 12
   100 µl of compounds at the 256 µg/ml working solution were added to column 1 (one compound per row)
   Two-fold serial dilutions were done from column 1 to 10
   Column 11 served as the growth control
5. The 10 organism panel was plated from stock vials stored at −80° C. and incubated for 24 hours at 34° C. The organisms were then sub-cultured and incubated for 24 hours at 34° C.
   The inoculums were first prepared in sterile distilled water with a target of 0.09-0.11 absorbance at 620 nm wavelength
   A 1/100 dilution was made into the appropriate broth
   100 µl of broth with organism was added to columns 1-11
   Column 12 served as the blank control
6. The completed 96 well plates were incubated for 24 hours at 34° C. The 96 well plates were then read using a Beckman Automated Plate Reader at 650 nm wavelength. The MIC was determined through calculations involving the growth control (column 11) and blank control (column 12).

Calculations

The absorbance readings from the Biomek Automated Plate Reader are used to determine the percent inhibition for each test well. The formula used is as follows:

$$\% \text{ Inhibition} = [1 - (ABS_{test} - ABS_{blank})/(ABS_{mean\ growth} - ABS_{blank})] \times 100\%$$

$ABS_{test}$: Absorbance of the test well
$ABS_{blank}$: Absorbance of the blank well in the same row as the test well (column 12)
$ABS_{mean\ growth}$: Mean absorbance of the growth control wells (column 11)

The minimum inhibitory concentration (MIC) is found at the lowest concentration of compound where percent inhibition is greater than or equal to 80%.

These procedures were used to obtain the representative microbiological data for the compounds 10 to 19 shown in Table 1 as MIC (Minimum Inhibitory Concentration) with the values expressed as micrograms per ml.

The compounds of this invention are evaluated for their antiviral activity as per the guidelines and procedures prescribed.

Protocols for Antiviral Determination

Yellow Fever (YFV) antiviral assay was performed with HeLa cells which were used in order to allow for a 7 day assay endpoint. HeLa cells were passaged in T-75 flasks. On the day preceding the assay, the cells were trypsinized, pelleted, counted and resuspended at $1 \times 10^4$/well in tissue culture medium in 96-well flat bottom tissue culture plates in a volume of 100 µl per well. One day following plating of cells, the wells were washed and the medium was replaced with complete medium (2% serum) containing various concentrations of test compound diluted in medium in a half-log series. A pretitered aliquot of 17D strain YFV virus was removed from the freezer (−80° C.) just before each experiment. The virus was diluted into tissue culture medium such that the amount of virus added to each well would give complete cell killing at 7 days post-infection.

HepG2 2.15 Antiviral Evaluation Assay—HepG2 2.2.15 cells, which produce HBV ayw1 strain, were plated in 96-well collagencoated microtiter plates at a density of $2.5 \times 10^4$/well with DMEM medium supplemented with 2% fetal bovine serum. One day following plating of cells, the wells were washed and the medium was replaced with complete medium containing the test compound diluted in the medium in a half-log series.

The medium was replaced once with the fresh medium containing the freshly diluted compound three days post the initial addition of the lamivudine, a positive control compound. Cell viability was determined using CellTiter 96® Reagent (Promega, Madison, Wis.) according to the manufacturer's protocol, using a Vmax plate reader (Molecular Devices, Sunnyvale, Calif.). The mixture is metabolized by the mitochondrial enzymes of metabolically active cells to a soluble formazan product, allowing the rapid quantitative analysis of cell numbers. The media was removed and replaced with 100 µl of fresh media and 10 µl of Cell Titer 96. Plates were reincubated for 4 hours at 37° C. and read spectrophotometrically at 490 and 650 nm with a Molecular Devices Vmax plate reader. Percent cell viability of compound treated wells compared to no compound controls was calculated using an in-house computer program which graphs the percent reduction in viral cytopathic effects and the cell numbers at each drug concentration relative to control values. The program interpolates the inhibitory concentration of drug that reduces cytopathic effects by 50% (IC50) and the toxic concentration that kills 50% of cells (TC50).

HCV RNA Replicon Antiviral Evaluation Protocol

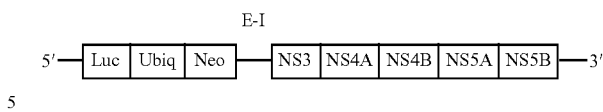

The cell line ET (luc-ubi-neo/ET), a new HCV RNA replicon that contains a stable luciferase (LUC) reporter, was used. The composition of the replicon is shown diagrammatically above (ref, Krieger, N., V. Lohmann, and R. Bartenschlager. 2001. Enhancement of hepatitis C virus RNA replicon replication by cell culture-adaptive mutations. J. Virol. 75:4614-4624). The HCV RNA replicon ET contains the 5' NTR (IRES) of HCV (5') which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV structural proteins NS3-NS5.

The NS3 protein cleaves the HCV polyprotein to release the mature NS3, NS4A, NS4B, NS5A and NS5B proteins that are required for HCV replication. At the 3' end of the replicon is the authentic 3' NTR of HCV. The LUC reporter is used as an indirect measure of HCV replication. The activity of the LUC reporter is directly proportional to HCV RNA levels and positive control antiviral compounds behave comparably using either LUC or RNA endpoints. The use of the LUC endpoint is more economical than HCV RNA and can be used for high-throughput applications to screen libraries of compounds.

The HCV RNA replicon antiviral evaluation assay examines the effects of compounds at five half-log concentrations each. Human interferon alpha-2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hr later when the cells are still subconfluent. Compound IC50 and IC90 values are derived from HCV RNA levels assessed as either HCV RNA replicon-derived LUC activity or as HCV RNA using TaqMan RT-PCR. Compound TC50 and TC90 values are calculated using a calorimetric assay as an indicator of cell numbers and cytotoxicity when the LUC assay system is employed, while ribosomal (rRNA) levels determined via TaqMan RTPCR are used as an indication of cell numbers in the RNA-based assay. Compound T150 and T190 values are calculated from spreadsheets.

Antibacterial Activity

Representative antibacterial data for the compounds 11 to 24 are shown in Table 1. The antibacterial activity of ciprofloxacin, cloxacillin, imipenem, ceftriaxone, meropenem, erythromycin and penicilling G, pertinent antibacterial-specific biological standards, are included as positive controls.

TABLE 1

Antibacterial Profile Against Select Gram-positive and Gram-negative Pathogens

| Exam | A | D | E | G | R* | M | N | S. aureus ATCC 29213 | S. epidermidis ATCC 12228 | S. pneumoniae ATCC 6301 | S. faecalis ATCC 29212 | S. faecium CT-26 |
|---|---|---|---|---|---|---|---|---|---|---|---|---|
| 11 | CH | C—F | CH | CH | 3-ClC$_6$H$_4$ | O | 1 | <0.125 | 1 | 8 | 32 | 32 |
| 12 | CH | CH | CH | CH | 3-ClC$_6$H$_4$ | O | 1 | 0.5 | 2 | 8 | 16 | 16 |
| 13 | CH | C—Cl | CH | CH | 3-FC$_6$H$_4$ | O | 1 | <0.125 | 0.25 | 4 | 16 | 8 |

TABLE 1-continued

Antibacterial Profile Against Select Gram-positive and Gram-negative Pathogens

| Exam | A | D | E | G | R* | M | N | S. aureus ATCC 29213 | S. epidermidis ATCC 12228 | S. pneumoniae ATCC 6301 | S. faecalis ATCC 29212 | S. faecium CT-26 |
|---|---|---|---|---|---|---|---|---|---|---|---|---|
| 14 | CH | CH | CH | CH | 3-NCC$_6$H$_4$ | O | 1 | 0.25 | 2 | 2 | 32 | 16 |
| 15 | CH | CH | C—F | CH | 3-ClC$_6$H$_4$ | O | 1 | 0.5 | 2 | 4 | 16 | 8 |
| 16 | CH | CH | CH | CH | 3-ClC$_6$H$_4$ | O | CMe$_2$ | 0.5 | 2 | 8 | 16 | 16 |
| 17 | CH | CH | CH | CH | 4-ClC$_6$H$_4$ | O | 1 | 2 | 2 | 4 | 16 | 16 |
| 18 | CH | CH | CH | CH | 4-NCC$_6$H$_4$ | O | 1 | 2 | 2 | 4 | 32 | 32 |
| 19 | CH | C—F | CH | CH | 4-NCC$_6$H$_4$ | O | 1 | 8 | 16 | 16 | >64 | >64 |
| 20 | CH | C—F | CH | CH | 3-NCC$_6$H$_4$ | O | 1 | 1 | 16 | 8 | 64 | 64 |
| 21 | CH | CH | C—F | CH | 3-NCC$_6$H$_4$ | O | 1 | 8 | 16 | 8 | 64 | 64 |
| 22 | CH | C—OMe | C—OMe | CH | 3-ClC$_6$H$_4$ | O | 1 | 4 | 16 | 8 | >64 | 64 |
| 23 | CH | CH | CH | CH | 3-ClC$_6$H$_4$ | O | 2 | 2 | 8 | 8 | 16 | 16 |
| 24 | CH | CH | CH | CH | 3-FC$_6$H$_4$ | O | 2 | 4 | 8 | 16 | 32 | 32 |
| | | | Ciprofloxacin | | | | | 0.125 | 0.125 | 0.5 | 0.5 | 64 |
| | | | Cloxacillin | | | | | 0.125 | 0.25 | 0.125 | 16 | 64 |
| | | | Imipenem | | | | | 0.125 | 0.125 | 0.125 | 1 | 64 |
| | | | Ceftriaxone | | | | | 2 | 1 | 0.125 | 64 | 64 |
| | | | Erythromycin | | | | | 0.5 | 0.5 | NA | 2 | NA |
| | | | Pen G | | | | | 0.5 | 16 | 0.125 | 1 | 32 |

Benzoxaborole Antivirals

This procedure was used to obtain the results in the following tables. Representative antiviral data for the compounds 11 to 22 are shown in Tables 2 and 3. The antiviral activity of interferon and lamividine, pertinent viral-specific biological standards, are included as positive controls.

TABLE 2

In vitro Antiviral Activity

| | Anti-Yellow Fever Activity | | | Anti-Hepatitis B Activity | | |
|---|---|---|---|---|---|---|
| Compound | IC50 (µM) | TC50 (µM) | Antiviral Index | IC50 (µM) | TC50 (µM) | Antiviral Index |
| 11 | 0.65 | 4.14 | 6.38 | 2.47 | 3.20 | 1.30 |
| 13 | 1.39 | 6.22 | 4.48 | NA | NA | NA |
| 14 | 0.44 | 6.53 | 14.91 | NA | NA | NA |
| 15 | 1.19 | 6.60 | 5.53 | NA | NA | NA |
| 17 | 1.56 | 6.42 | 4.11 | NA | NA | NA |
| 18 | 0.74 | 6.60 | 8.91 | NA | NA | NA |
| 19 | NA | 17.1 | NA | NA | NA | NA |
| 20 | 1.62 | 21.0 | 12.98 | NA | NA | NA |
| 21 | 2.36 | 15.8 | 6.72 | NA | NA | NA |
| 22 | NA | 21.1 | NA | NA | NA | NA |
| IFN-alpha | 3.20 IU | >1000 IU | >312.5 | NA | NA | NA |
| lamivudine | NA | NA | NA | 0.0093 | >1.0 | >107.5 |

TABLE 3

In vitro Anti-Hepatitis Activity (Replicon Assay)

| Compound | IC50 (µM) | TC50 (µM) | Selectivity Index |
|---|---|---|---|
| 11 | 12.96 | 1.29 | 1.5 |
| 12 | 30.6 | 12.7 | 2.4 |
| 13 | 3.93 | 0.37 | 11 |
| 14 | 2.86 | 1.14 | 2.5 |
| 15 | 6.01 | 0.54 | 11 |
| 17 | 8.59 | 0.26 | 33 |
| 18 | 1.94 | NA | NA |
| 19 | 3.73 | 0.27 | 14 |
| 20 | 19.53 | 5.99 | 3.2 |
| 21 | 5.48 | 0.69 | 7.9 |
| IFN-alpha2b | >5.00 (IU/ml) | 0.08 (IU/ml) | >82.5 |

Boron-Containing Therapeutics

The synthesis of the compounds of the invention is accomplished in several formats. Scheme #1 demonstrates an efficient synthesis of the benzoxaboroles, with broad range of substituents, including analogs (M=O, S, NR**) and the larger ring analogs. This is in contrast to the procedure of Haynes and Snyder [J. Org. Chem., 29, pp. 3229-3233 (1964) which is limited in scope. Intermediate 1, after transmetallation by either Grignard exchange (isopropylmagnesium bromide) or an organolithium (preferably sec-butyllithium or tert-butyllithium), is reacted with a trialkyl borate. Subsequent acidic hydrolysis affords an intermediates boronic acid 2. Conversion of 2 to the ethylene glycol boronate 3 is achieved in high yields. Other diols such as 1,2-propanediol, 1,3-propanediol, 1,2-butanediol, 1,3-butanediol, 1,4-butanediol, or pinacol alcohol can be employed. Boronate esters 3 are reacted with the appropriate organometallic donor of substituent R*, followed by acidic hydrolysis to afford the desired benzoxaboroles 5.

While we demonstrate the use of the methoxymethyl (MOM) protecting group in the examples, other suitable protecting groups can be employed; exemplary are trialkylsilyl, alkyldiarylsilyl, tetrahydropyranyl, trialkylsilylalkoxy, trityl and substituted trityls, and tert-butyl.

The corresponding benzoazaboroles 7 and benzothiaboroles 9 were similarly obtained from suitably protected precursors.

Scheme 1

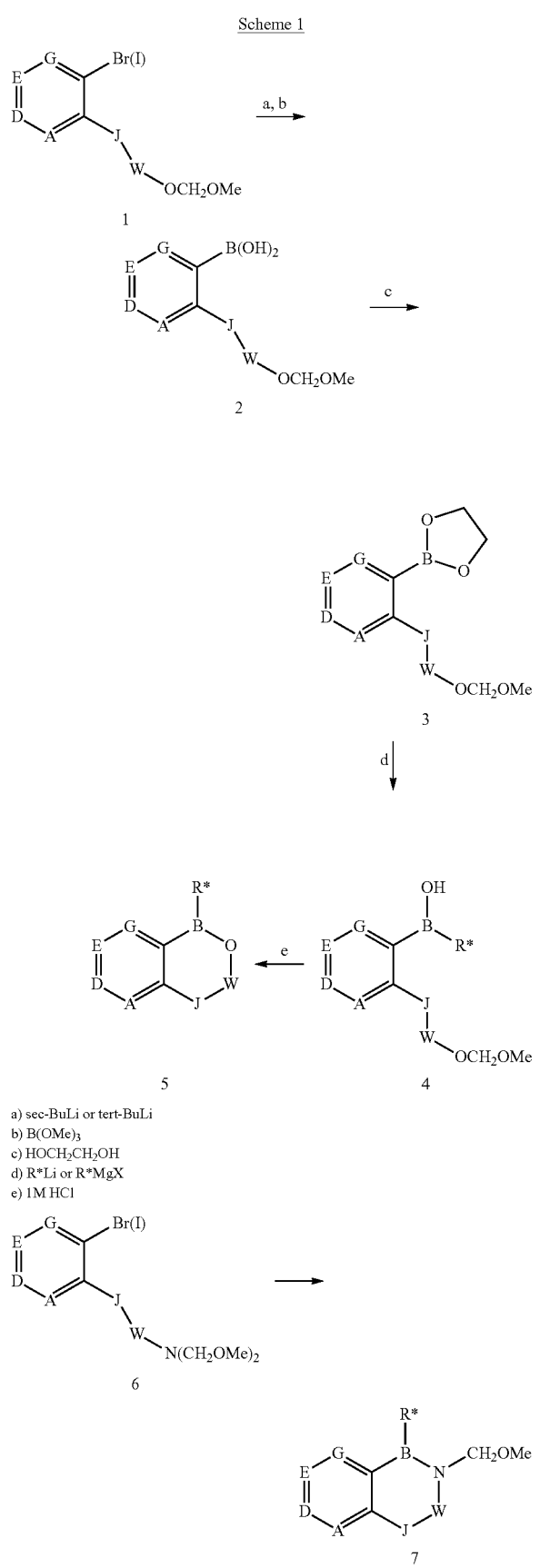

a) sec-BuLi or tert-BuLi
b) B(OMe)₃
c) HOCH₂CH₂OH
d) R*Li or R*MgX
e) 1M HCl

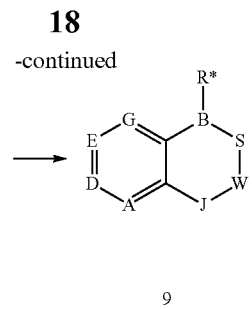

In certain situations, compounds of the invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention include, but are not limited to the compounds disclosed herein and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. In a preferred embodiment, the compounds of the invention comprise any of compounds 11-24 (Tables 1 to 3), and variants thereof.

The present invention also encompasses the acylated prodrugs of the compounds of the invention. Those skilled in the art will recognize various synthetic methodologies which may be employed to prepare non-toxic pharmaceutically acceptable addition salts and acylated prodrugs of the inventive compounds.

EXAMPLES

Proton NMR are recorded on Varian AS 400 spectrometer and chemical shifts are reported as δ (ppm) down field from tetramethylsilane. Mass spectra are determined on Micromass Quattro II.

1-(3-Chlorophenyl)-5-fluoro-1,3-dihydrobenzo[c][1,2]oxaborole (11)

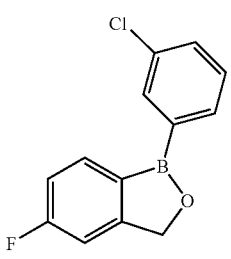

a) 2-(3-Chlorophenyl)-[1,3,2]-dioxaborolane: 3-Chlorophenylboronic acid (3.041 g, 19.4 mmol) was dissolved in 75 mL of dry THF under $N_2$. Ethylene glycol (1.323 g, 21.3 mmol) was added and the solution refluxed for 18 hours. The solution was allowed to cool and the THF removed under vacuum. The residue was further dried under high vacuum (<1 mmHg) with occasional heating to remove excess ethylene glycol and THF. This gave pure 2-(3-chlorophenyl)[1,3,2]-dioxaborolane (3.55 g, 100%) as a brown oil that solidified upon cooling in the freezer: $^1$H NMR δ 4.39 (s, 4H), 7.32 (t, 1H), 7.44 (ddd, 1H), 7.67 (d, 1H), 7.78 (d, 1H).

b) 2-Bromo-5-fluorobenzyl alcohol: 2-Bromo-5-fluorobenzaldehyde (2.05 g, 10.1 mmol) was dissolved in 20 mL of warm absolute ethanol. Upon cooling to room temperature, sodium borohydride (0.19 g, 5.0 mmol) was slowly added to the ethanol solution. The solution was stirred at room temperature for 18 hours. 1 mL of $H_2O$ was added to the solution and the ethanol removed under vacuum. The white residue was then partitioned between 30 mL of $H_2O$ and 50 mL of diethyl ether. The ether was separated and the aqueous solution extracted twice more with ether (2×50 mL). The ether extracts were combined, dried with $MgSO_4$, filtered and evaporated to give pure 2-bromo-5-fluorobenzyl alcohol as a white solid (1.98 g, 96%): $^1$H NMR δ1.98 (t, 1H), 4.72 (d, 2H), 6.89 (dt, 1H), 7.27 (dd, 1H), 7.48 (dd, 1H).

c) 1-Bromo-4-fluoro-2-((methoxymethoxy)methyl)benzene: Sodium hydride (60% dispersion in mineral oil, 0.225 g, 5.6 mmol) was placed in a 250 mL round bottom flask under $N_2$. The NaH was washed with dry hexanes (5 mL). The hexanes were removed via cannula, and the process repeated twice (2×5 mL). The NaH was dried under vacuum until a free flowing powder resulted and placed under $N_2$. (2-Bromo-5-fluorophenyl)methanol (0.97 g, 4.7 mmol) was dissolved in 20 mL of dry THF and added dropwise to the solid NaH. Once H2 evolution had ceased, the solution was refluxed for 1.5 hours. The solution was allowed to cool to room temperature then cooled to 0° C. in an ice bath. Chloromethyl methyl ether (0.36 mL, 4.2 mmol) was then added and the solution allowed to warm to room temperature. The solution was stirred at room temperature for 18 hours then filtered through a 1 cm column of Celite. The Celite was washed with THF (2×10 mL). The THF filtrates were combined and evaporated under vacuum to give pure 1-bromo-4-fluoro-2-((methoxymethoxy)methyl)benzene as an oil (1.05 g, 99%): $^1$H NMR δ 3.49 (s, 3H), 4.63 (s, 2H), 4.78 (s, 2H), 6.88 (dt, 1H), 7.26 (dd, 1H), 7.49 (dd, 1H).

d) (3-Chlorophenyl)(4'-fluoro-(2'-(methoxymethoxy)methyl)phenyl)borinic acid: 1-Bromo-4-fluoro-2-((methoxymethoxy)methyl)benzene (1.06 g, 4.2 mmol) was dissolved in 50 mL of dry THF under $N_2$ and cooled to −78° C. t-BuLi (1.7M in pentane)(5.3 mL, 9.0 mmol) was slowly added to the solution. After stirring for 10 minutes at −78° C., 2-(3-chlorophenyl)-[1,3,2]-dioxaborolane in 10 mL of dry THF was added and the solution stirred for a further 0.5 hours. The solution was then allowed to warm to room temperature and stirred for 18 hours. The THF was removed under vacuum and the residue partitioned between 40 ml of $H_2O$ and 80 mL of diethyl ether. The solution was vigorously stirred for several minutes then neutralized (pH7) with 6N HCl. The ether was separated and the aqueous solution extracted again with ether (2×80 mL). The ether extracts were combined, dried with $MgSO_4$, filtered and evaporated to give a yellow oil (1.22 g). $^1$H NMR of the product shows that the desired borinic acid was formed. This was used for the next step without purification.

Note: The borinic acid could be purified by flash column chromatography on silica gel using 3:1 hexanes:ethyl acetate as eluent. However, this leads to significant loss of desired product. Subsequent reactions showed that purification at this step was not necessary. $^1$H NMR δ 3.45 (s, 3H), 4.65 (s, 2H), 4.66 (s, 2H), 7.06-7.12 (2H), 7.34 (t, 1H), 7.44 (ddd, 1H), 7.52 (dd, 1H), 7.63 (td, 1H), 7.73 (d, 1H), 8.00 (s, 1H).

e) 1-(3-Chlorophenyl)-5-fluoro-1,3-dihydrobenzo[c][1,2] oxaborole: The MOM protected borinic acid (0.70 g, 2.3 mmol) was dissolved in 46 mL of THF and 4 mL of concentrated HCl. The solution was stirred at room temperature for 12 hours. 10 mL of $H_2O$ was then added and the THF removed under vacuum. This gave a solid suspension. The solid was filtered under vacuum and washed with water (10 mL) then with hexanes (5 mL) and dried. This gave titled compound as a white solid (0.334 g, 59%): $^1$H NMR δ 5.38 (s, 2H), 7.14-7.19 (2H), 7.43 (t, 1H), 7.52 (td, 1H), 8.00 (d, 1H), 8.08 (d, 1H), 8.13 (dd, 1H); MS (ES$^-$) 247.08, 249.03 (3:1); HPLC [ret. Time (% area)] 14.346 min (97.1%).

1-(3-Chlorophenyl)-1,3-dihydrobenzo[c][1,2]oxaborole (12)

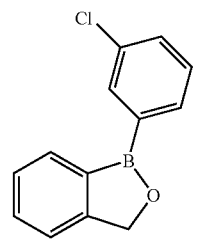

This was prepared as per the procedure in Example 11, from 2-(3-chlorophenyl)-[1,3,2]-dioxaborolane and 1-bromo-2-((methoxymethoxy)methyl)benzene to afford white crystalline product.

5-Chloro-1-(3-Fluorophenyl)-1,3-dihydrobenzo[c][1,2]oxaborole (13)

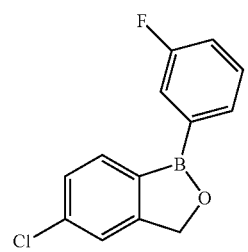

This was prepared as per the procedure in Example 11, from 2-(3-fluorophenyl)-[1,3,2]-dioxaborolane and 1-bromo-4-chloro-2-((methoxymethoxy)methyl)benzene to afford white crystalline product.

3-(Benzo[c][1,2]oxaborol-1(3H)-yl)benzonitrile (14)

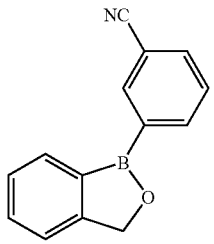

This was prepared as per the procedure in Example 11, from 2-(3-cyanophenyl)[1,3,2]-dioxaborolane and 1-bromo-2-((methoxymethoxy)methyl)benzene to afford white crystalline product.

1-(3-Chlorophenyl)-6-fluoro-1,3-dihydrobenzo[c][1,2]oxaborole (15)

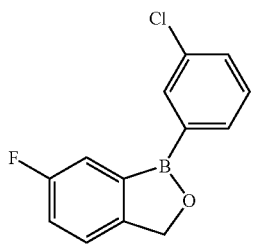

a) 2-Bromo-4-fluorobenzyl alcohol: 2-Bromo-4-fluorobenzoic acid (7.908 g, 36.1 mmol) was dissolved in 50 mL of dry THF under $N_2$ and cooled to 0° C. $BH_3$-THF (1M in THF) (72 mL, 72 mmol) was added dropwise with stirring. Once the vigorous effervescence had subsided, the solution was stirred for a further 0.5 hours at 0° C. then allowed to warm to room temperature. The solution was stirred at room temperature for 18 hours. The THF was removed under vacuum and the residue dissolved in $CH_2Cl_2$ (100 mL). Methanol was slowly added to the solution until no bubbling could be observed and the solution was stirred for a further 15 minutes. The solvents were removed under vacuum and the residue re-dissolved in methanol (100 mL). The solution was stirred for 10 minutes then the solvent was removed under vacuum. The residue was further dried for several hours under high vacuum (<1 mmHg). This gave pure 2-bromo-4-fluorobenzyl alcohol as a pale yellow solid (7.33 g, 99%): $^1$H NMR δ 1.99 (s, 1H), 4.72 (s, 3H), 7.05 (dt, 1H), 7.31 (dd, 1H), 7.46 (dd, 1H).

b) 2-Bromo-4-fluoro-1-((methoxymethoxy)methyl)benzene: Sodium hydride (60% dispersion in mineral oil, 0.39 g, 9.7 mmol) was placed in a 250 mL round bottom flask under $N_2$. The NaH was washed with dry hexanes (5 mL). The hexanes were removed via cannula, and the process repeated twice (2×5 mL). The NaH was dried under vacuum until a free flowing powder resulted and placed under $N_2$. (2-Bromo-4-fluorophenyl)methanol (1.61 g, 7.8 mmol) was dissolved in 30 mL of dry THF and added dropwise to the solid NaH. Once $H_2$ evolution had ceased, the solution was refluxed for 1 hour. The solution was allowed to cool to room temperature then cooled to 0° C. in an ice bath. Chloromethyl methyl ether (0.6 mL, 7.9 mmol) was then added and the solution allowed to warm to room temperature. The solution was stirred at room temperature for 18 hours then filtered through a 1.5 cm column of Celite. The Celite was washed with THF (2×10 mL). The THF filtrates were combined and evaporated under vacuum to give pure 2-bromo-4-fluoro-1-((methoxymethoxy)methyl)benzene as an oil (1.700 g, 87%): $^1$H NMR δ 3.43 (s, 3H), 4.63 (s, 2H), 4.75 (s, 2H), 7.04 (dt, 1H), 7.31 (dd, 1H), 7.46 (dd, 1H).

d) (3-Chlorophenyl)(5'-fluoro-(2'-(methoxymethoxy)methyl)phenyl)borinic acid: 2-Bromo-4-fluoro-1-((methoxymethoxy)methyl)benzene (1.70 g, 6.8 mmol) was dissolved in 50 mL of dry THF under $N_2$ and cooled to −78° C. t-BuLi (1.7 M in pentane)(8.5 mL, 14.5 mmol) was slowly added to the solution. After stirring for 15 minutes at −78° C., 2-(3-chlorophenyl)-[1,3,2]-dioxaborolane in 10 mL of dry THF was added and the solution stirred for a further 0.5 hours. The solution was then allowed to warm to room temperature and stirred for 18 hours. The THF was removed under vacuum and the residue partitioned between 50 mL of $H_2O$ and 80 mL of diethyl ether. The solution was vigorously stirred for several minutes then neutralized (pH=7) with 6N HCl. The ether was separated and the aqueous solution extracted again with ether (2×50 mL). The ether extracts were combined, dried with $MgSO_4$, filtered and evaporated to give an orange oil (2.27 g). $^1$H NMR of the product showed that the desired borinic acid was formed. This was used for the next step without purification.

e) 1-(3-Chlorophenyl)-6-fluoro-1,3-dihydrobenzo[c][1,2] oxaborole: The crude MOM protected borinic acid (2.27 g) was dissolved in 46 mL of THF and 4 mL of concentrated HCl. The solution was stirred at room temperature for 12 hours. 10 mL of $H_2O$ was then added and the THF removed under vacuum. The aqueous solution was extracted with diethyl ether (3×50 mL). The ether extracts were combined and washed with brine until neutral. The ether was dried with $MgSO_4$, filtered and evaporated to give an orange oil. The crude product was purified by column chromatography on silica gel using 5:1 hexanes:ethyl acetate as eluent. After removal of the solvents, titled compound (Rf=0.63) was obtained as a white solid (0.515 g, 2.1 mmol. 33%; two steps): $^1$H NMR δ 5.39 (s, 2H), 7.24-7.29 (2H), 7.42-7.48 (2H), 7.53 (ddd, 1H), 7.78 (dd, 1H), 7.99 (d, 1H), 8.07 (d, 1H); MS (ES$^-$) 290.95, 292.97 (3:1) [Note: M$^-$+formic acid]; HPLC [ret. Time (% area)] 14.162 min (97.6%).

1-(3-Chlorophenyl)-1,3-dihydro-3,3-dimethylbenzo[c][1,2]oxaborole (16)

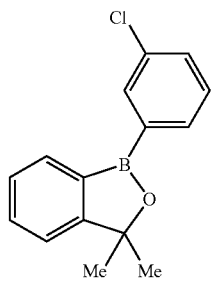

a) 2-(2-Bromophenyl)propan-2-ol: Methyl-2-bromobenzoate (3.403 g, 15.8 mmol) was dissolved in 50 mL of dry THF under $N_2$ and cooled to 0° C. Methyl magnesium iodide (3M in diethyl ether) (11 mL, 33 mmol) was added and the solution allowed to warm to room temperature followed by reflux for 1 hour. 50 mL of saturated ammonium chloride was added and the solution filtered under vacuum. The separated solids were washed with THF. The THF filtrates were combined and the solvent was removed under vacuum. The residue was partitioned between 40 mL of $H_2O$ and 60 mL of diethyl ether with stirring. The ether was separated and the aqueous solution was extracted twice more with ether (2×60 mL). The ether extracts were combined and washed with brine until neutral. The ether was dried with $MgSO_4$, filtered and evaporated to give a yellow oil. The crude product was purified by column chromatography on silica gel using $CHCl_3$ as eluent. After removal of the solvent, pure 2-(2-bromophenyl)propan-2-ol (Rf=0.33) was obtained as a yellow oil (2.55 g, 75%): $^1$H NMR δ 1.75 (s, 6H), 2.79 (s, 1H), 7.10 (dt, 1H), 7.30 (dt, 1H), 7.58 (dd, 1H), 7.66 (dd, 1H).

b) 1-Bromo-2-(2-(methoxymethoxy)propan-2-yl)benzene: Sodium hydride (60% dispersion in mineral oil, 0.576 g, 14.4 mmol) was placed in a 250 mL round bottom flask under $N_2$. The NaH was washed with dry hexanes (10 mL). The hexanes were removed via cannula, and the process repeated twice (2×10 mL). The NaH was dried under vacuum until a free flowing powder resulted and placed under $N_2$. 2-(2-bromophenyl)propan-2-ol (2.55 g, 11.8 mmol) was dissolved in 50 mL of dry THF and added dropwise to the solid NaH. Once $H_2$ evolution had ceased, the solution was refluxed for 1.5 hours. The solution was allowed to cool to room temperature then cooled to 0° C. in an ice bath. Chloromethyl methyl ether (0.82 mL, 10.8 mmol) was then added and the solution allowed to warm to room temperature. The solution was stirred at room temperature for 18 hours then filtered through a 1 cm column of Celite. The Celite was washed with THF (2×15 mL). The THF filtrates were combined and evaporated under vacuum to give a brown oil. The crude product was purified by column chromatography on silica gel using 2:1 hexanes:ethyl acetate as eluent. After removal of the solvents, pure 1-bromo-2-(2-(methoxymethoxy)propan-2-yl)benzene (Rf=0.82) was obtained as a yellow oil (1.70 g, 55%): $^1$H NMR δ 1.77 (s, 6H), 3.14 (s, 3H), 4.62 (s, 2H), 7.10 (dt, 1H), 7.28 (dt, 1H), 7.50 (dd, 1H), 7.62 (dd, 1H).

c) (3-Chlorophenyl)(2-(2-(methoxymethoxy)propan-2-yl)phenylborinic acid: 2-Bromo-2-(2-(methoxymethoxy)propan-2-yl)benzene (1.700 g, 6.5 mmol) was dissolved in 50 mL of dry THF under $N_2$ and cooled to −78° C. t-BuLi (1.7M in pentane)(8.4 mL, 14.3 mmol) was slowly added to the solution. After stirring for 15 minutes at −78° C., 2-(3-chlorophenyl)-[1,3,2]dioxaborolane in 10 mL of dry THF was added and the solution stirred for a further 0.5 hours. The solution was then allowed to warm to room temperature and stirred for 18 hours. The THF was removed under vacuum and the residue partitioned between 50 mL of $H_2O$ and 80 mL of diethyl ether. The solution was vigorously stirred for several minutes then neutralized (pH7) with 6N HCl. The ether was separated and the aqueous solution extracted again with ether (2×50 mL). The combined ether extracts were combined, dried with $MgSO_4$, filtered and evaporated to give an orange oil (2.13 g). The crude product was purified by column chromatography on silica gel using 3:1 hexanes:ethyl acetate as eluent. After removal of the solvents, pure borinic acid (Rf=0.80) was obtained as a yellow oil (0.87 g, 42%): $^1$H NMR δ 1.61 (s, 6H), 3.39 (s, 3H), 4.57 (s, 2H), 7.19-7.55 (5H), 8.02-8.11 (3H).

e) 1-(3-Chlorophenyl)-1,3-dihydro-3,3-dimethylbenzo[c][1,2]oxaborole: The crude MOM protected borinic acid (0.87 g, 2.7 mmol) was dissolved in 46 mL of THF and 4 mL of concentrated HCl. The solution was stirred at room temperature for 12 hours. 10 mL of $H_2O$ was then added and the THF removed under vacuum. The aqueous solution was extracted with diethyl ether (3×60 mL). The ether extracts were combined and washed with brine until neutral. The ether was dried with $MgSO_4$, filtered and evaporated to give a yellow oil. The crude product was purified by column chromatography on silica gel using 5:1 hexanes:ethyl acetate as eluent. After removal of the solvents, titled compound (Rf=0.67) was obtained as a yellow oil (0.29 g, 41%): $^1$H NMR δ 1.64 (s, 6H), 7.37 (d, 1H), 7.40-7.45 (2H), 7.48-7.55 (2H), 8.03 (td, 1H), 8.07-8.11 (2H); MS (ES$^-$) 301.01, 303.02 (3:1) [Note: M$^-$+formic acid]; HPLC [ret. Time (% area)] 15.847 min (92.2%).

1-(4-Chlorophenyl)-1,3-dihydrobenzo[c][1,2]oxaborole (17)

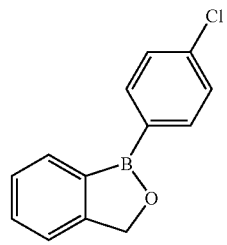

This was prepared as per the procedure in Example 11, from 2-(4-chlorophenyl)-[1,3,2]-dioxaborolane and 1-bromo-2-((methoxymethoxy)methyl)benzene to afford white crystalline product.

4-(Benzo[c][1,2]oxaborol-1(3H)-yl)benzonitrile (18)

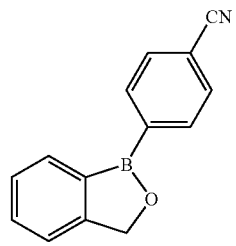

This was prepared as per the procedure in Example 11, from 2-(4-cyanophenyl)-[1,3,2]-dioxaborolane and 1-bromo-2-((methoxymethoxy)methyl)-benzene to afford white crystalline product.

4(5-Fluorobenzo[c][1,2]oxaborol-1(3H)-yl)benzonitrile (19)

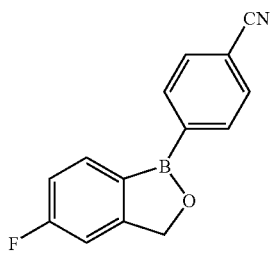

This was prepared as per the procedure in Example 11, from 2-(4-cyanophenyl)-[1,3,2]-dioxaborolane and 1-bromo-4-fluoro-2-((methoxymethoxy)methyl)benzene to afford white crystalline product.

3-(5-Fluorobenzo[c][1,2]oxaborol-1(3H)-yl)benzonitrile (20)

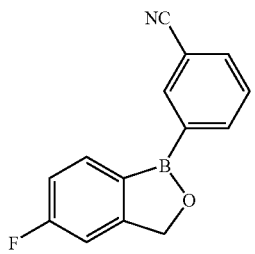

This was prepared as per the procedure in Example 11, from 2-(3-cyanophenyl)-[1,3,2]-dioxaborolane and 1-bromo-4-fluoro-2-((methoxymethoxy)methyl)benzene to afford white crystalline product.

3-(6-Fluorobenzo[c][1,2]oxaborol-1(3H)-yl)benzonitrile (21)

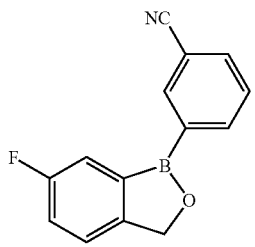

This was prepared as per the procedure in Example 11, from 2-(3-cyanophenyl)-[1,3,2]-dioxaborolane and 1-bromo-5-fluoro-2-((methoxymethoxy)methyl)benzene to afford white crystalline product.

1-(3-Cyanophenyl)-5,6-dimethoxy-1,3-dihydrobenzo[c][1,2]-oxaborole (22)

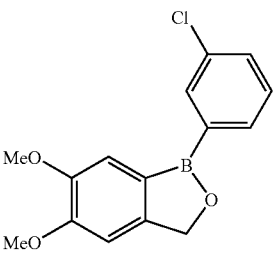

This was prepared as per the procedure in Example 11, from 2-(3-chlorophenyl)-[1,3,2]-dioxaborolane and 1-bromo-4,5-dimethoxy-2-((methoxymethoxy)methyl)-benzene to afford white crystalline product.

(4-(5-(Fluorobenzo[c][1,2]oxaborol-1(3H)-yl)phenylmethanamine (23)

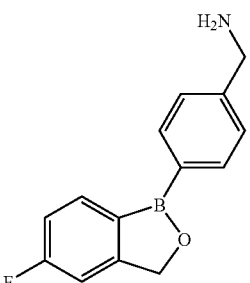

a) N,N-Bis(methoxymethyl)-4-bromobenzylamine: To a solution of 4-bromobenzylamine hydrochloride (4.54 g, 20.0 mmol) in methanol (200 mL) were added 37% formaldehyde (25 mL) and potassium carbonate (4.28 g, 31.0 mmol), and the mixture was stirred at room temperature for overnight. The mixture was concentrated under reduced pressure to a third of volume. Water was added and the mixture was extracted with ethyl acetate. The organic layer was washed with brine and dried on anhydrous sodium sulfate. The solvent was removed under reduced pressure to afford N,N-bis(methoxymethyl)-4-bromobenzylamine (5.45 g, 99%): $^1$H NMR (300 MHz, CDCl$_3$) δ 3.26 (s, 6H), 3.94 (s, 4H), 4.20 (s, 2H), 7.21 (d, J=8.2 Hz, 2H), 7.44 (d, J=8.5 Hz, 2H).

b) 1-Bromo-4-fluoro-2-((methoxymethoxy)methyl)benzene: To a solution of 2-bromo-5-fluorobenzoic acid (10.3 g, 45.3 g) in tetrahydrofuran (50 mL) was added borane-tetrahydrofuran complex (1M in tetrahydrofuran; 92 mL) at 0° C. under nitrogen atmosphere, and the mixture was stirred at room temperature overnight. Water was carefully added, and the mixture was concentrated under reduced pressure to about 50 mL. Water was added and the mixture was extracted with ethyl acetate. The organic layer was washed with brine and dried on anhydrous sodium sulfate. The solvent was removed under reduced pressure to afford 2-bromo-5-fluorobenzyl alcohol, which was converted into its methoxymethyl ether in a similar manner to Example 11, step (a) to afford 1-bromo- 4-fluoro-2-((methoxymethoxy)methyl)benzene (9.64 g, 85% in 2 steps): $^1$H NMR (300 MHz, CDCl$_3$) δ 3.43 (s, 3H), 4.62 (s, 2H), 4.78 (s, 2H), 6.88 (td, J=8.5, 3.2 Hz, 1H), 7.25 (dd, J=9.6, 3.1 Hz, 1H), 7.48 (dd, J=8.8, 5.3 Hz, 1H).

c) 5-Fluoro-2-(methoxymethoxymethyl)phenyl-[1,3,2]-dioxaborolane: This was obtained from the above intermediate: $^1$H NMR (300 MHz, CDCl$_3$) δ 3.42 (s, 3H), 4.36 (s, 4H), 4.76 (s, 2H), 4.87 (s, 2H), 6.96 (td, J=8.2, 2.6 Hz, 1H), 7.26 (dd, J=10.6, 2.6 Hz, 1H), 7.83 (dd, J=8.2, 6.4 Hz, 1H).

d) (4-(5-(Fluorobenzo[c][1,2]oxaborol-1(3H)-yl)phenyl-methanamine: The title compound was obtained from N,N-bis(methoxymethyl)-4-bromobenzylamine and 5-fluoro-2-[(methoxymethoxymethyl)phenyl]-[1,3,2]-dioxaboralane: $^1$H NMR (300 MHz, DMSO-d$_6$) δ 3.72 (s, 2H), 5.29 (s, 2H), 7.15 (m, 1H), 7.3-7.5 (m, 3H), 7.96 (d, J=7.6 Hz, 1H), 8.11 (dd, J=8.2, 5.9 Hz, 1H): ESI-MS m/z 242 (positive); C$_{14}$H$_{13}$BFNO=241.

(3-(5-(Fluorobenzo[c][1,2]oxaborol-1(3H)-yl)-phenylmethanamine (24)

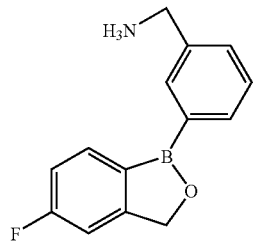

The title compound was obtained from 3-bromobenzylamine hydrochloride in a similar sequence as Example 23: $^1$H NMR (300 MHz, DMSO-d$_6$) δ 3.74 (s, 2H), 5.32 (s, 2H), 7.1-7.5 (m, 4H), 7.86 (d, J=7.6 Hz, 1H), 7.98 (s, 1H), 8.12 (dd, J=8.2, 5.9 Hz, 1H): ESI-MS m/z 242 (positive); C$_{14}$H$_{13}$BFNO=241.

(4-(5-(Fluorobenzo[c][1,2]oxaborol-1(3H)-yl)phenyl)methanol (25)

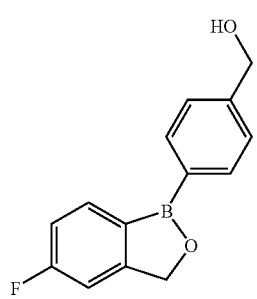

The title compound was obtained from 4-bromobenzyl alcohol in a similar sequence described in Examples 11 and 23: $^1$H NMR (300 MHz, DMSO-d$_6$) δ 4.56 (d, J=5.0 Hz, 2H), 5.25 (t, J=5.6 Hz, 1H), 5.37 (s, 2H), 7.26 (m, 1H), 7.4-7.5 (m, 3H), 8.05 (d, J=7.9 Hz, 1H), 8.22 (dd, J=8.2, 5.9 Hz, 1H): ESI-MS m/z 241 (negative); C$_{14}$H$_{12}$BFO$_2$=242.

(3-(5-(Fluorobenzo[c][1,2]oxaborol-1(3H)-yl)phenyl)methanol (26)

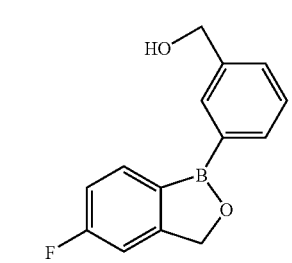

The title compound was obtained from 3-bromobenzyl alcohol in a sequence similar to Examples 11 and 23: $^1$H NMR (300 MHz, DMSO-d$_6$) δ 4.57 (d, J=5.6 Hz, 2H), 5.22 (t, J=5.6 Hz, 1H), 5.37 (s, 2H), 7.26 (m, 1H), 7.4-7.5 (m, 3H), 8.03 (s, 1H), 8.20 (dd, J=8.2, 5.9 Hz, 1H): ESI-MS m/z 241 (negative); C$_{14}$H$_{12}$BFO$_2$=242.

3-(6-Fluorobenzo[c][1,2]oxaborol-1(3H)-yl)phenol (27)

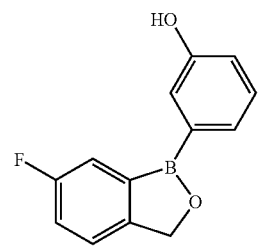

The title compound was obtained from 3-bromophenol and 2-bromo-4-fluorobenzoic acid in a similar manner to Examples 11 and 23: $^1$H NMR (300 MHz, DMSO-d$_6$) δ 5.30 (s, 2H), 6.89 (d, J=8.2 Hz, 1H), 7.25 (t, J=7.6 Hz, 1H), 7.33 (t, J=8.9 Hz, 1H), 7.41 (s, 1H), 7.45 (d, J=7.0 Hz, 1H), 7.55 (dd, J=8.4, 4.9 Hz, 1H), 7.73 (d, J=8.8 Hz, 1H), 9.31 (s, 1H): ESI-MS m/z 227 (negative); C$_{13}$H$_{10}$BFO$_2$=228.

3-(5-Fluorobenzo[c][1,2]oxaborol-1(3H)-yl)pyridine (28)

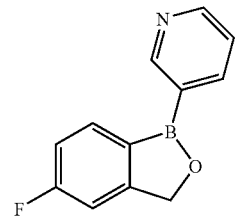

To a solution of 3-bromopyridine (731 mg, 4.63 mmol) in tetrahydrofuran was added isopropylmagnesium chloride (1 mol/L; 2.3 mL) at room temperature under nitrogen atmosphere, and the mixture was stirred for 1 h. To the mixture was added 5-fluoro-2-[(methoxymethoxymethyl)phenyl]-[1,3,2]-dioxaborolane obtained in Example 23, step (c) (11.1 g, 4.63 mmol) in tetrahydrofuran (4 mL), and the mixture was stirred at room temperature for overnight. Water was added and the pH was adjusted to pH7 with 1M hydrochloric acid. Then the mixture was extracted with ethyl acetate. The solvent was removed under reduced pressure, and the residue was dissolved in tetrahydrofuran (30 mL). To the mixture was added 1M hydrochloric acid (10 mL), and the mixture was refluxed for overnight. The pH was adjusted to 7 with saturated sodium bicarbonate and the mixture was extracted with ethyl acetate. The organic layer was washed with brine and dried on anhydrous sodium sulfate. The solvent was removed under reduced pressure and the residue was recrystallized from diisopropyl ether to afford the title compound (76 mg, 7.7%): $^1$H NMR (300 MHz, DMSO-$d_6$) δ 4.94 (s, 2H), 6.9-7.1 (m, 2H), 7.36 (br s, 1H), 7.66 (dd, J=6.7, 5.3 Hz, 1H), 8.19 (d, J=6.7 Hz, 1H), 8.24 (br s, 1H), 8.64 (d, J=5.3 Hz, 1H): ESI-MS m/z 214 (positive); $C_{12}H_9BFNO=213$.

(2-(Benzo[c][1,2]oxaborol-1(3H)-yl)phenyl)methanol (29)

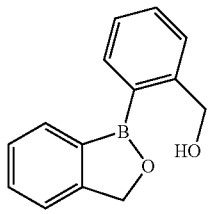

a) 1-Bromo-2-((methoxymethoxy)methyl)benzene: To solution of 2-bromobenzyl alcohol (10.0 g, 53.5 mmol) and diisopropylethylamine (11 mL, 64 mmol) in dichloromethane (150 mL) was added chloromethyl methyl ether (4.5 mL, 59 mmol) at 0° C. under nitrogen atmosphere, and the mixture was stirred at room temperature for 15 h. Water was added, and the mixture was extracted with chloroform. The organic layer was washed with brine and dried on anhydrous sodium sulfate. The solvent was removed under reduced pressure, and the residue was purified by silica gel column chromatography (12:1 hexane/ethyl acetate) to give 1-bromo-2-((methoxymethoxy)methyl)benzene (11.7 g, 95%); $^1$H NMR (300 MHz, CDCl$_3$) δ 3.44 (s, 3H), 4.67 (s, 2H), 4.77 (s, 2H), 7.16 (td, J=7.9, 1.8 Hz, 1H), 7.32 (td, J=7.3, 1.2 Hz, 1H), 7.49 (dd, J=7.9, 1.8 Hz, 1H), 7.55 (dd, J=8.2, 1.2 Hz, 1H).

b) 2-[(Methoxymethoxy)methyl]phenylboronic acid: 1-Bromo-2-(methoxy-methoxy)methylbenzene (2.50 g, 10.8 mmol) in tetrahydrofuran (25 mL) was added sec-butyllithium (1.4 mol/L in cyclohexane; 9.3 mL) at −78° C. under nitrogen atmosphere. After stirring for 15 min, trimethyl borate (2.5 mL, 22 mol) was added dropwise, and the mixture was stirred at room temperature for 16 h. Water and 1M hydrochloric acid were added, and the mixture was extracted with ethyl acetate. The organic layer was washed with brine and dried on anhydrous sodium sulfate. The solvent was removed under reduced pressure and the residue was purified by silica gel column chromatography (2:1 hexane/ethyl acetate) to give desired boronic acid (1.47 g, 69%).

c) 2-[(Methoxymethoxymethyl)phenyl]-[1,3,2]-dioxaborolane: Mixture of 2-[(methoxymethoxy)methyl]phenyl-boronic acid (1.47 g, 7.50 mmol), ethylene glycol (466 mg, 7.50 mmol), and toluene (50 mL) was heated at reflux in a Dean-Stark apparatus for 3 h. The solvent was removed under reduced pressure to give desired boronate ester (1.59 g, 95%): $^1$H NMR (300 MHz, CDCl$_3$) δ 3.42 (s, 3H), 4.37 (s, 4H), 4.75 (s, 2H), 4.87 (s, 2H), 7.30 (td, J=7.3, 2.1 Hz, 1H), 7.4-7.5 (m, 2H), 7.84 (d, J=7.9 Hz, 1H).

d) Bis [2-(methoxymethoxymethyl)phenyl]borinic acid: A solution of 1-bromo-2-((methoxymethoxy)methyl)benzene obtained in step (a) (1.65 g, 7.16 mmol) in tetrahydrofuran (14 mL) was added sec-butyllithium (1.4M in cyclohexane; 6.2 mL) at −78° C. under nitrogen atmosphere. After stirring for 15 min, a solution of 2-[(Methoxymethoxymethyl)phenyl]-[1,3,2]-dioxaborolane obtained in step (c) (1.59 g, 7.16 mmol) in tetrahydrofuran (7 mL) was added, and the mixture was stirred at room temperature for 1 h. Water and 1M hydrochloric acid were added, and the mixture was extracted with ethyl acetate. The organic layer was washed with brine and dried on anhydrous sodium sulfate. The solvent was removed under reduced pressure to afford desired borinic acid (1.82 g, 77%).

e) (2-(Benzo[c][1,2]oxaborol-1(3H)-yl)phenyl)methanol: To a solution of the above compound (1.38 g, 4.18 mmol) in tetrahydrofuran (60 mL) was added 1M hydrochloric acid (20 mL), and the mixture was refluxed for 5 h. The mixture was concentrated under reduced pressure to about half volume. The precipitates formed were collected by filtration to afford the title compound (610 mg, 65%): $^1$H NMR (300 MHz, DMSO-$d_6$) δ 4.98 (s, 4H), 7.1-7.4 (m, 8H); ESI-MS m/z 223 (negative); $C_{14}H_{13}BO_2=224$ (2-(Benzo[c][1,2]oxaborol-1(3H)-yl)phenyl)-N,N-dimethylmethanamine (30)

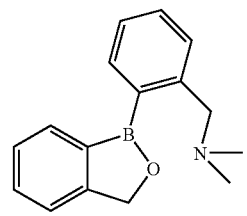

To a solution of (2-(benzo[c][1,2]oxaborol-1(3H)-yl)phenyl)methanol (300 mg, 1.34 mmol) in dichloromethane (10 mL) were added sequentially triethylamine (0.373 mL, 2.7 mmol) and methanesulfonyl chloride (0.125 mL, 1.60 mmol) at 0° C. After stirring for 30 min, dimethylamine (2M in tetrahydrofuran; 3 mL) was added, and the mixture was stirred for another 30 min. Water was added and the mixture was extracted with ethyl acetate. The organic layer was washed with brine and dried on anhydrous sodium sulfate. The solvent was removed under reduced pressure and the residue was purified by silica gel column chromatography (1:2 hexane/ethyl acetate) followed by recrystallization from diisopropyl ether/hexane to give the title compound (185 mg, 55%): $^1$H NMR (300 MHz, DMSO-$d_6$) δ 2.25 (s, 3H), 2.41 (s, 3H), 4.09 (br d, J=8.5 Hz, 2H), 4.87 (d, J=13.2 Hz, 1H), 5.05 (d, J=13.2 Hz, 1H), 7.0-7.3 (m, 8H); ESI-MS m/z 252 (positive); $C_{16}H_{18}BNO=251$ (2-(Benzo[c][1,2]oxaborol-1(3H)-yl)-5-chlorophenyl)-N,N-dimethylmethanamine (31)

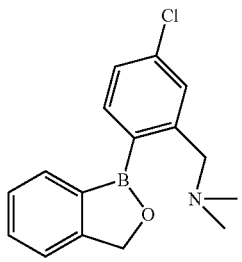

a) 2-Bromo-5-chlorobenzyl bromide: A mixture of 2-bromo-5-chlorotoluene (12.0 g, 56.6 mmol), N-bromosuccinimide (11.1 g, 62.3 mmol), and 2,2'-azobisisobutyronitrile (464 mg, 2.83 mmol) in carbon tetrachloride (220 mL) was stirred at 50° C., 60° C., 70° C., and reflux for 30 min each. After cooling down to room temperature, water was added, and the mixture was extracted with chloroform. The organic layer was washed with brine and dried on anhydrous sodium sulfate. The solvent was removed under reduced pressure to afford 2-bromo-5-chlorobenzyl bromide (17.1 g): $^1$H NMR (300 MHz, CDCl$_3$) δ 4.53 (s, 2H), 7.15 (dd, J=8.5, 2.3 Hz, 1H), 7.45 (d, J=2.3 Hz, 1H), 7.50 (d, J=8.8 Hz, 1H).

b) 1-Bromo-2-(dimethylamino)methyl-4-chlorobenzene: To a solution of the above compound (5.00 g, 17.6 mmol) in tetrahydrofuran (10 mL) was added dimethylamine (2M in tetrahydrofuran; 20 mL), and the mixture was stirred at room temperature for 2 h. Water was added, and the mixture was extracted with ethyl acetate. The organic layer was washed with brine and dried on anhydrous sodium sulfate. The solvent was removed under reduced pressure to afford 1-bromo-2-(dimethylamino)methyl-4-chlorobenzene (2.32 g, 53%): $^1$H NMR (300 MHz, CDCl$_3$) δ 2.30 (s, 6H), 3.48 (s, 2H), 7.09 (dd, J=7.9, 2.6 Hz, 1H), 7.45 (d, J=8.2 Hz, 1H), 7.46 (d, J=2.6 Hz, 1H).

c) (2-(Benzo[c][1,2]oxaborol-1(3H)-yl)-5-chlorophenyl)-N,N-dimethylmethanamine To a solution of 1-bromo-2-(dimethylamino)methyl-4-chlorobenzene (1.00 g, 4.02 mmol) in tetrahydrofuran (8 mL) was added sec-butyllithium (1.4M in cyclohexane; 3.6 mL) at −78° C. under nitrogen atmosphere. After stirring for 15 min, to the mixture was added 2-[(methoxymethoxymethyl)phenyl]-[1,3,2]dioxaborolane (892 mg, 4.02 mmol) in tetrahydrofuran (4 mL), and the mixture was stirred for overnight while warming up to room temperature. Water was added, and the mixture was washed with ethyl acetate. The pH was adjusted to pH7 with 1M hydrochloric acid, and the mixture was extracted with ethyl acetate. The organic layer was washed with brine and dried on anhydrous sodium sulfate. The solvent was removed under reduced pressure. The residue was dissolved in tetrahydrofuran (60 mL) and 1 mol/L hydrochloric acid (20 mL) was added. The mixture was refluxed for 2 h. After cooling down to room temperature, water and saturated sodium bicarbonate were added, and the mixture was extracted with ethyl acetate. The organic layer was washed with brine and dried on anhydrous sodium sulfate. The solvent was removed under reduced pressure and the residue was purified by silica gel column chromatography (2:3 to 1:2 hexane/ethyl acetate) followed by trituration with diisopropyl ether to give the title compound (356 mg, 31% in 2 steps): $^1$H NMR (300 MHz, DMSO-d$_6$) δ 2.25 (s, 3H), 2.41 (s, 3H), 4.10 (d, J=3.8 Hz, 2H), 4.88 (d, J=14.1 Hz, 1H), 5.05 (d, J=14.1 Hz, 1H), 7.0-7.3 (m, 7H): ESI-MS m/z 288, 286 (positive); $C_{16}H_{17}B^{35}ClNO=285$ (2-(Benzo[c][1,2]oxaborol-1(3H)-yl)-5-chlorophenyl)methanol (32)

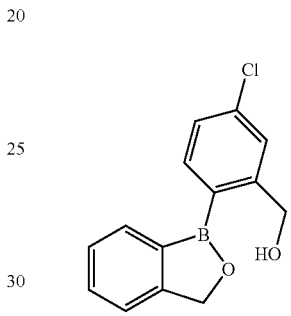

a) 2-Bromo-5-chlorobenzyl alcohol: Solution of 2-bromo-5-chlorobenzyl bromide (12.1 g, 42.6 mmol), sodium acetate (16.4 g, 200 mmol), and dimethylformamide (120 mL) was stirred at 70° C. for overnight. After cooling down to room temperature, water was added and the mixture was extracted with ethyl acetate. The organic layer was washed with brine and dried on anhydrous sodium sulfate. The solvent was removed under reduced pressure and the residue was dissolved in methanol (160 mL). To the mixture was added 1M sodium hydroxide (40 mL), and the mixture was refluxed for 2 h. The mixture was concentrated under reduced pressure to about half volume. Then water was added and the mixture was extracted with ethyl acetate. The organic layer was washed with brine and dried on anhydrous sodium sulfate. The solvent was removed under reduced pressure and the residue was triturated with hexane to give desired alcohol (5.00 g, 53% in 2 steps): $^1$H NMR (300 MHz, DMSO-d$_6$) δ 4.47 (d, J=5.6 Hz, 2H), 5.57 (t, J=5.6 Hz, 1H), 7.26 (dd, J=8.5, 2.9 Hz, 1H), 7.50 (d, J=2.6 Hz, 1H), 7.58 (d, J=8.5 Hz, 1H).

b) 1-Bromo-4-chloro-2-((methoxymethoxy)methyl)benzene: The above alcohol was converted into its methoxymethyl ether in the similar manner to Example 11, step (a) to afford 1-bromo-4-chloro-2-((methoxy-methoxy)methyl)benzene: $^1$H NMR (300 MHz, CDCl$_3$) δ 3.43 (s, 3H), 4.62 (s, 2H), 4.77 (s, 2H), 7.13 (dd, J=8.5, 2.6 Hz, 1H), 7.46 (d, J=8.5 Hz, 1H), 7.50 (d, J=2.6 Hz, 1H).

c) (2-(Benzo[c][1,2]oxaborol-1(3H)-yl)-5-chlorophenyl)methanol: Title compound was obtained from the above intermediate (b) and 2-[(methoxymethoxymethyl)phenyl]-[1,3,2]-dioxaborolane: $^1$H NMR (300 MHz, DMSO-d$_6$) δ 4.92 (s, 2H), 5.00 (s, 2H), 7.1-7.4 (m, 7H): ESI-MS m/z 259, 257 (negative); $C_{14}H_{12}B^{35}ClO_2$=258.

(5-Chloro-2-(5-chlorobenzo[c][1,2]oxaborol-1(3H)-yl)phenyl)methanol (33)

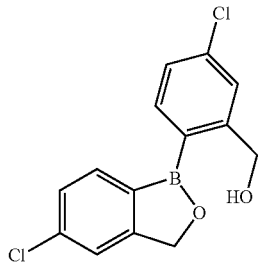

a) Bis[4-chloro-2-(methoxymethoxymethyl)phenyl] borinic acid: To a solution of 1-bromo-4-chloro-2-((methoxymethoxy)methyl)benzene (3.62 g, 13.6 mmol) in tetrahydrofuran (27 mL) was added sec-butyllithium (1.4 mol/L in cyclohexane; 12 mL) at −78° C. under nitrogen atmosphere. After stirring for 15 min, to the mixture was added trimethyl borate (706 mg, 6.8 mmol) in tetrahydrofuran (5 mL) and the mixture was stirred at room temperature for overnight. Water and 1 mol/L hydrochloric acid were added, and the mixture was extracted with ethyl acetate. The organic layer was washed with brine and dried on anhydrous sodium sulfate. The solvent was removed under reduced pressure and the residue was purified by silica gel column chromatography (3:1~2:1 hexane/ethyl acetate) to give desired acid (880 mg, 32%).

b) (5-Chloro-2-(5-chlorobenzo[c][1,2]oxaborol-1(3H)-yl)phenyl)methanol: The title compound was obtained from the above compound in a similar manner to Example 11, step (e) after purification by silica gel column chromatography (9:1 chloroform/methanol): $^1$H NMR (300 MHz, DMSO-$d_6$) δ 4.93 (s, 4H), 7.18 (m, 4H), 7.32 (m, 2H): ESI-MS m/z 295, 293, 291 (negative); $C_{14}H_{11}B^{35}Cl_2O_2$=292.

(5-Chloro-2-(5-chlorobenzo[c][1,2]oxaborol-1(3H)-yl)phenyl-N,N-dimethylmethanamine (34)

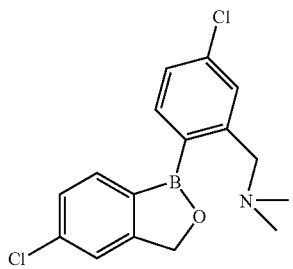

Title compound was obtained from (5-chloro-2-(5-chlorobenzo[c]-[1,2]oxaborol-1(3H)-yl)phenyl)methanol: $^1$H NMR (300 MHz, DMSO-$d_6$) δ 2.26 (s, 3H), 2.42 (s, 3H), 4.11 (d, J=2.9 Hz, 2H), 4.86 (d, J=14.7 Hz, 1H), 5.03 (d, J=14.3 Hz, 1H), 7.03 (d, J=7.6 Hz, 1H), 7.1-7.2 (m, 3H), 7.2-7.3 (m, 2H): ESI-MS m/z 324, 322, 320 (positive); $C_{16}H_{16}B^{35}Cl_2NO$=319.

1-(4-chloro-2-methoxyphenyl)-1,3-dihydrobenzo[c][1,2]benzoxaborole (35)

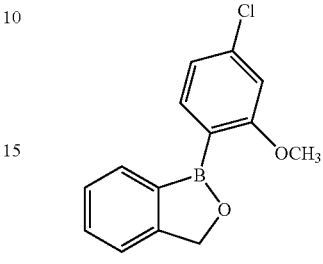

a) 4-Chloro-2-methoxyphenylboronic acid ethylene glycol ester: To a solution of 2-bromo-5-chloroanisole (4.43 g, 20 mmol) in dry THF (100 mL) at −78° C. was added dropwise t-BuLi (14.1 mL, 1.7 M, 23.97 mmol). The mixture was stirred for 10 min at −78° C. and trimethyl borate (2.23 mL, 20 mmol) was added. The cooling bath was removed and the mixture was stirred for 30 min from −78° C. to room temperature and then for 3 h with a water bath. Hydrochloric acid (6N, 8 mL) and brine were added. The mixture was extracted with ethyl acetate, dried and evaporated to give 4-chloro-2-methoxyphenylboronic acid as a brown solid (3.33 g, 17.88 mmol) in 89.4% yield. This boronic acid was mixed with ethylene glycol (1.1 g, 17.88 mmol) and toluene (150 mL). The mixture was refluxed for 2 h under $N_2$ with the help of a Dean-Stark trap to remove water generated. After being cooled to room temperature, the solution was transferred to another dry flask and rotary evaporated to provide 4-Chloro-2-methoxyphenylboronic acid ethylene glycol ester as a brown liquid (3.6 g, 16.97 mmol) in 84.8% yield.

b) 1-(4-chloro-2-methoxyphenyl)-1,3-dihydrobenzo[c][1,2]benzoxaborole: To a solution of 2-(methoxymethoxymethyl)phenyl bromide (3.929 g, 17 mmol), which was obtained as described in Example 11(a), in dry THF (150-200 mL) at −78° C. was added dropwise t-BuLi (12 mL, 1.7 M, 20.4 mmol). The mixture was stirred for 10 min at −78° C. and a solution of 4-chloro-2-methoxyphenylboronic acid ethylene glycol ester (3.6 g, 17 mmol) in THF (30 mL) was added resulting in a viscous mixture. The cooling bath was removed and the mixture was stirred for 30 min from −78° C. to room temperature and then for 3 h with a water bath. Hydrochloric acid (6N, 12 mL) was added and the mixture was stirred briefly for 5 min. The aqueous layer was removed and the THF layer was rotary evaporated. The residue was mixed with THF (50 mL), methanol (50 mL) and 6N HCl (50 mL) giving a homogeneous solution that was stirred for 30 min at room temperature. Organic solvents were rotary evaporated and the residue was extracted with ethyl acetate (3×80 mL). The combined ethyl acetate solution was washed with brine, dried and evaporated. The residue was purified by flash column chromatography eluted with a mixed solvent of hexanes and ethyl acetate (6:1, v/v) to provide 1,3-dihydro-1-(4-chloro-2-methoxyphenyl)-2,1-benzoxaborole as a white solid (AN-2551, 2.63 g, 10.17 mmol) in 59.8% yield. M.p. 66-68° C.; $^1$H NMR (DMSO-$d_6$, 300 MHz): δ 8.05 (dm, J=7.2 Hz, 1H), 7.80 (dd, $J_1$=7.8 Hz, $J_2$=2.1 Hz, 1H), 7.52-7.50 (m, 2H), 7.40-7.36 (m, 1H), 7.15-7.13 (m, 1H), 7.06 (dt, $J_1$=8.1 Hz, $J_2$=2.1 Hz, 1H), 5.34 (s, 2H) and 3.904 & 3.898 (s & s, 3H) ppm.

2-(Benzo[c][1,2]oxaboral-1(3H)-yl)-5-chlorophenol (36)

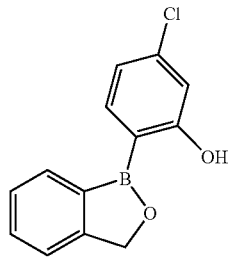

To a solution of 1,3-dihydro-1-(4-chloro-2-methoxyphenyl)-2,1-benzoxaborole as a white solid (AN-2551, 0.5 g, 1.93 mmol) in anhydrous methylene chloride (25 mL) at −78° C. was added dropwise a solution of boron tribromide in methylene chloride (1.0 M, 1.93 mL, 1.93 mmol) under nitrogen. The mixture was stirred at −78° C. for 1 h and at room temperature for 4 h. Then the reaction flask was recooled to −78° C. and methanol (10 mL) was added. The reaction mixture was warmed to room temperature and 6N HCl (2 mL) was added. The mixture was evaporated to give a residue that was mixed with ethyl acetate. The organic layer was washed with brine, dried and evaporated. The residue was purified by flash column chromatography eluted with a mixed solvent of hexanes and ethyl acetate (4:1, v/v) to provide the desired compound 1,3-dihydro-1-(4-chloro-2-hydroxyphenyl)-2,1-benzoxaborole as a white solid (0.32 g, 1.31 mmol) in 67.8% yield. M.p. 96-98° C.; $^1$H NMR (MeOH-$d_4$, 300 MHz): δ 8.19 (d, J=7.5 Hz, 1H), 7.92 (d, J=8.1 Hz, 1H), 7.52-7.51 (m, 2H), 7.43-7.38 (m, 1H), 6.96-6.91 (m, 1H), 6.89-6.88 (m, 1H) and 5.41 (s, 2H) ppm.

2-(3-(Benzo[c][1,2]oxaborol-1(3H)-yl)phenoxy)-5-chlorophenol (37)

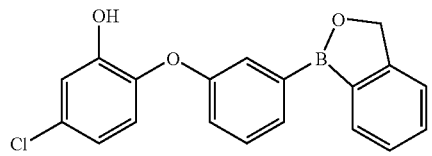

a) 3-(4-Chloro-2-methoxyphenoxy)phenyl bromide: To a three-necked flask equipped with a thermometer, a condenser-topped Dean-Stark trap and a rubber septa were added 4-chloro-2-methoxyphenol (10 g, 63.05 mmol), 1,3-dibromobenzene (14.88 g, 63.05 mmol), copper powder (0.4 g, 6.3 mmol) and potassium hydroxide (5 g, 75.7 mmol). Under nitrogen atmosphere, the mixture was stirred and heated slowly to 220-230° C. and kept at this temperature for 1 h. After being cooled to room temperature, methylene chloride was added and the mixture was filtered. The filtrate was washed with 10% NaOH (2×200 mL), dried and evaporated. The residue was purified by flash column chromatography over silica gel eluted with a mixed solvent of hexanes and EtOAc (6:1, v/v) to provide 3-(4-chloro-2-methoxyphenoxy) phenyl bromide as a liquid-solid mixed form (3.09 g, 9.85 mmol) in 15.6% yield. $^1$H NMR (DMSO-$d_6$, 300 MHz): δ 7.29-7.20 (m, 3H), 7.12 (dd, $J_1$=8.4 Hz, $J_2$=1.2 Hz, 1H), 7.05-7.00 (m, 2H), 6.85-6.81 (m, 1H) and 3.75 (s, 3H) ppm.

b) 3-(4-Chloro-2-hydroxyphenoxy)phenyl bromide: The demethylation procedure used in Example 37 was adapted for the synthesis of 3-(4-chloro-2-hydroxyphenoxy)phenyl bromide from 3-(4-chloro-2-methoxyphenoxy)phenyl bromide. The crude product was purified by flash column chromatography eluted with a mixed solvent of hexanes and EtOAc (6:1, v/v) to give 3-(4-chloro-2-hydroxyphenoxy)phenyl bromide as a white solid in 100% yield. M.p. 63-65° C.; MS (ESI, negative): m/z=299 (M-1); $^1$H NMR (DMSO-$d_6$, 300 MHz): δ 10.21 (s, 1H), 7.28-7.19 (m, 2H), 7.05 (d, J=9.0 Hz, 1H), 6.99-6.97 (m, 2H) and 6.89-6.82 (m, 2H) ppm.

c) 3-(4-Chloro-2-methoxymethoxyphenoxy)phenyl bromide: The methoxymethyl protection procedure used in Example 11 (a) was adapted for the synthesis of 3-(4-chloro-2-methoxymethoxyphenoxy)phenyl bromide from 3-(4-chloro-2-hydroxyphenoxy)phenyl bromide. The crude product was purified by flash column chromatography eluted with a mixed solvent of hexanes and ethyl acetate (5:1, v/v) to afford 3-(4-chloro-2-methoxymethoxyphenoxy)phenyl bromide as a colorless oil in 84.5% yield. $^1$H-NMR (DMSO-$d_6$, 300 MHz): δ 7.33-7.01 (m, 6H), 6.89-6.85 (m, 1H), 5.18 (s, 2H) and 3.21 (s, 3H) ppm.

d): 2-(3-(Benzo[c][1,2]oxaborol-1(3H)-yl)Phenoxy)-5-chlorophenol The procedure used for the preparation of Example 36 from 2-(methoxy-methoxy)methylphenyl bromide and 4-chloro-2-methoxyphenylboronic acid ethylene glycol ester was adapted for the synthesis of the title compound from 3-(4-chloro-2-methoxymethoxyphenoxy)phenyl bromide and 2-[(methoxy-methoxy)methyl]phenylboronic acid ethylene glycol ester. The crude product was purified by flash column chromatography over silica gel eluted with a mixed solvent of hexanes and EtOAc (4:1, v/v). The solid obtained was washed with n-pentane and hexanes (50:50, v/v) to give 1,3-dihydro-1-[3-(4-chloro-2-hydroxyphenoxy) phenyl]-2,1-benzoxaborole as a white solid in 28.5% yield. M.p. 115-117° C.; $^1$H NMR (MeOH-$d_4$, 300 MHz): δ 8.05 (d, J=7.2 Hz, 1H), 7.85 (d, J=6.9 Hz, 1H), 7.64 (d, J=2.1 Hz, 1H), 7.52 (d, J=3.9 Hz, 2H), 7.47-7.38 (m, 2H), 7.11 (dd, $J_1$=8.1 Hz, $J_2$=2.1 Hz, 1H), 6.98 (d, J=2.4 Hz, 1H), 6.91 (d, J=8.7 Hz, 1H), 6.83 (dd, $J_1$=8.4 Hz, $J_2$=2.4 Hz, 1H) and 5.35 (s, 2H) ppm. The title compound can alternatively be prepared by lithium exchange of 3-(4-chloro-2-methoxyphenoxy)phenyl bromide and then reacting with 2-[(methoxymethoxy)methyl]phenylboronic acid ethylene glycol ester to give the corresponding methylated analogue of the title compound. Demethylation of this analogue can generate the desired title compound.

4-((3-(5-Fluorobenzo[c][1,2]oxaborol-1(3H)-yl)phenyl)methyl)morpholine (38)

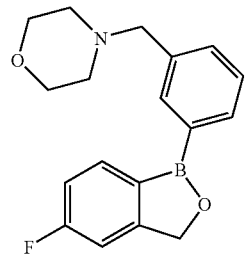

The title compound was obtained from (3-(5-(fluorobenzo[c][1,2]oxaborol-1(3H)-yl)phenyl)methanol obtained in Example 27 and morpholine. It was dissolved in ether and treated solution of 0.25M fumaric acid in methanol. The solvent was removed under reduced pressure and the residue was triturated with diisopropyl ether to afford the title compound as fumarate salt: $^1$H NMR (300 MHz, DMSO-$d_6$) δ 2.41 (m, 4H), 3.57 (m, 4H), 5.33 (s, 2H), 6.60 (s, 1H), 7.23 (t, J=9.1 Hz, 1H), 7.3-7.5 (m, 3H), 7.94 (m, 2H), 8.12 (dd, J=7.6, 6.5 Hz, 1H): ESI-MS m/z 312 (positive); $C_{18}H_{19}BFNO_2$=311.

(3-(5-Fluorobenzo[c][1,2]oxaborol-1(3H)-yl]phenyl)-methyl 8-hydroxy-quinoline-2-carboxylate (39)

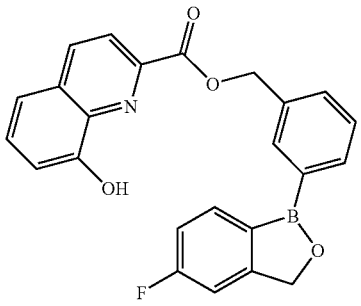

A mixture of (3-(5-(fluorobenzo[c][1,2]oxaborol-1(3H)-yl)-phenyl)methanol from Example 27 (100 mg, 0.413 mmol), 8-hydroxyquinoline-2-carboxylic acid (156 mg, 0.826 mmol), 1-(3-dimethylaminopropyl)-3-ethylcarbodiimide (159 mg, 0.826 mmol), 1-hydroxybenzotriazole (112 mg, 0.826 mmol), and 4-N,N-dimethylaminopyridine (101 mg, 0.826 mmol) in dimethylformamide (3 mL) was stirred at room temperature for overnight. Water was added and the mixture was extracted with ethyl acetate. The organic layer was washed with brine and dried on anhydrous sodium sulfate. The solvent was removed under reduced pressure and the residue was purified by silica gel column chromatography (1:1 hexane/ethyl acetate) followed by recrystallization from ethyl acetate/hexane to give the title compound (92 mg, 54%): $^1$H NMR (300 MHz, DMSO-$d_6$) δ 5.34 (s, 2H), 5.54 (s, 2H), 7.1-7.2 (m, 2H), 7.36 (dd, J=9.6, 2.0 Hz, 1H), 7.4-7.6 (m, 3H), 7.67 (d, J=7.6 Hz, 1H), 8.01 (d, J=7.3 Hz, 1H), 8.1-8.2 (m, 3H), 8.47 (d, J=8.5 Hz, 1H), 10.0 (s, 1H): ESI-MS m/z 414 (positive), 412 (negative); $C_{24}H_{17}BFNO_4$=413.

1-(3-Chlorophenyl)-2,3-dihydro-2-(methoxymethy)-1H-benzo[c][1,2]azaborole (40)

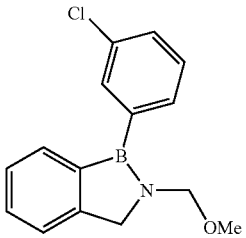

a) N,N-Bis(methoxymethyl)-2-bromobenzylamine: A solution of 2-bromobenzylamine hydrochloride (4.85 g, 20.7 mmol) in methanol (200 mL) was added 37% formaldehyde (25 mL) and potassium carbonate (4.28 g, 31.0 mmol), and the mixture was stirred at room temperature overnight. The mixture was evaporated under reduced pressure to a third of volume. Water was added and the mixture was extracted with ethyl acetate. The organic layer was washed with brine and dried on anhydrous sodium sulfate. The solvent was removed under reduced pressure to afford N,N-bis(methoxymethyl)-2-bromobenzylamine (5.76 g, quant): $^1$H NMR (300 MHz, CDCl$_3$) δ 3.28 (s, 6H), 4.11 (s, 2H), 4.26 (s, 4H), 7.12 (td, J=7.6, 1.8 Hz, 1H), 7.28 (td, J=7.3, 0.9 Hz, 1H), 7.43 (dd, J=7.6, 1.8 Hz, 1H), 7.55 (dd, J=7.9, 1.2 Hz, 1H).

b) 3-Chlorophenyl 2-[N,N-bis(methoxymethyl)aminomethyl]phenylborinic acid: To a solution of the above compound (2.74 g, 10.0 mmol) in tetrahydrofuran (20 mL) was added sec-butyllithium (1.4 mol/L in cyclohexane; 10 mL) at −78° C. under nitrogen atmosphere. After stirring for 15 min, to the mixture was added 3-chlorophenyl-[1,3,2]-dioxaborolane (1.82 g, 10.0 mmol) in tetrahydrofuran (8 mL), and the mixture was stirred at room temperature for 2 h. Water and 1M hydrochloric acid were added, and the mixture was extracted with ethyl acetate. The organic layer was washed with brine and dried on anhydrous sodium sulfate. The solvent was removed under reduced pressure to afford 3-chlorophenyl 2-[N,N-bis(methoxymethyl)aminomethyl]phenylborinic acid (2.57 g, 77%).

c) 1-(3-Chlorophenyl)-2,3-dihydro-2-(methoxymethy)-1H-benzo[c][1,2]azaborole: To a solution of the above compound (1.00 g, 4.18 mmol) in ethanol (27 mL) was added conc. hydrochloric acid (3 mL), and the mixture was refluxed for overnight. Saturated sodium bicarbonate was added and the mixture was extracted with ethyl aceate. The organic layer was washed with brine and dried on anhydrous sodium sulfate. The solvent was removed under reduced pressure and the residue was purified by silica gel column chromatography (9:1 chloroform/methanol) to give the title compound (550 mg, 68%): $^1$H NMR (300 MHz, DMSO-$d_6$) δ 3.03 (s, 3H), 3.9-4.2 (m, 2H), 5.94 (br s, 2H), 7.0-7.3 (m, 7H).

1-(3-Chlorophenyl)-1,3,4,5-tetrahydrobenzo-[c][1,2]-oxaborepine (41)

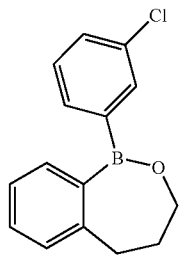

a) 3-(2-Bromophenyl)propan-1-ol: 3-(2-Bromophenyl) propionic acid (4.989 g, 21.8 mmol) was dissolved in 50 mL of dry THF under $N_2$ and cooled to 0° C. BH$_3$-THF (1M in THF) (40 mL, 40 mmol) was added dropwise with stirring. Once the vigorous effervescence had subsided, the solution was stirred for a further 0.5 hours at 0° C. then allowed to warm to room temperature.

The solution was stirred at room temperature for 18 hours. The THF was removed under vacuum and the residue dissolved in CH$_2$Cl$_2$ (100 mL). Methanol was slowly added to the solution until no bubbling could be observed and the solution was stirred for a further 15 minutes. The solvents were removed under vacuum and the residue redissolved in methanol (100 mL). The solution was stirred for 10 minutes then the solvent was removed under vacuum. The residue was further dried for several hours under high vacuum (<1 mmHg). This gave pure 3-(2-bromophenyl)-propan-1-ol as a yellow oil (4.54 g, 97%): $^1$H NMR δ 1.90 (tt, 2H), 2.84 (t, 2H), 3.71 (t, 2H), 7.06 (m, 1H), 7.24 (m, 2H), 7.53 (d, 1H).

b) 1-Bromo-2-(2-(methoxymethoxy)propyl)benzene: 3-(2-Bromophenyl)propan-1-ol (2.123 g, 9.9 mmol) was dissolved in 50 mL of CH$_2$Cl$_2$ at room temperature under N$_2$. Diisopropylethylamine (1.9 mL, 11.9 mmol) and chloromethyl methyl ether (0.82 mL, 10.8 mmol) were then added and the solution was stirred at room temperature for 18 hours. The reaction mixture was poured into a separatory funnel and extracted with H$_2$O (2×20 mL) followed by brine (1×20 mL). The CH$_2$Cl$_2$ was dried with MgSO$_4$, filtered and evaporated under vacuum to give pure 1-bromo-2-(2-(methoxymethoxy)propyl)benzene as a yellow oil (2.45 g, 96%): $^1$H NMR δ 1.92 (tt, 2H), 2.83 (t, 2H), 3.39 (s, 3H), 3.58 (t, 2H), 4.65 (s, 2H), 7.06 (m, 1H), 7.24 (m, 2H), 7.53 (d, 1H).

c) 1-(3-Chlorophenyl)-1,3,4,5-tetrahydrobenzo[c][1,2]oxaborepine: 2-Bromo-2-(3-methoxymethoxypropyl)benzene (1.212 g, 4.7 mmol) was dissolved in 50 mL of dry THF under N$_2$ and cooled to −78° C. t-BuLi (1.7M in pentane)(6.0 mL, 10.2 mmol) was slowly added to the solution. After stirring for 15 minutes at −78° C., 2-(3-chloro-phenyl)-[1,3,2]dioxaborolane was added and the solution stirred for a further 0.5 hours. The solution was then allowed to warm to room temperature and stirred for 18 hours. 5 ml of concentrated HCl was then added and the solution stirred at room temperature for a further 24 hours. 10 mL of H$_2$O was then added and the THF removed under vacuum. The aqueous solution was extracted with diethyl ether (3×50 mL). The ether extracts were combined and washed with brine until neutral. The ether was dried with MgSO$_4$, filtered and evaporated to give an orange oil. The crude product was purified by column chromatography on silica gel using 5:1 hexanes:ethyl acetate as eluent. After removal of the solvents, titled compound (Rf=0.82) was obtained as a yellow oil (0.480 g, 40%): $^1$H NMR δ 2.18 (tt, 2H), 2.81 (t, 2H), 4.11 (t, 2H), 7.24 (d, 1H), 7.29-7.36 (2H), 7.40-7.49 (3H), 7.73 (td, 1H), 7.84 (m, 1H); MS (ES$^-$) no molecular ion observed; HPLC [ret. Time (% area)] 15.573 min (96.9%).

1-(3-Chlorophenyl)-3,4-dihydro-1H-benzo[c][1,2]-oxaborinine (42)

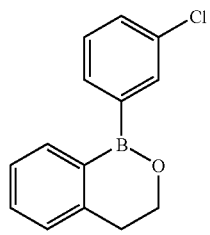

a) 2-(3-Chlorophenyl)-[1,3,2]dioxaborolane: 3-Chlorophenyl boronic acid (3.041 g, 19.4 mmol) was dissolved in 75 mL of dry THF under N$_2$. Ethylene glycol (1.323 g, 21.3 mmol) was added and the solution refluxed for 18 hours. The solution was allowed to cool and the THF removed under vacuum. The residue was further dried under high vacuum (<1 mmHg) with occasional heating to remove excess ethylene glycol and THF. This gave pure 2-(3-chlorophenyl)-[1,3,2]dioxaborolane (3.55 g, 100%) as a brown oil that solidified upon cooling in the freezer: $^1$H NMR δ 4.39 (s, 4H), 7.32 (t, 1H), 7.44 (ddd, 1H), 7.67 (d, 1H), 7.78 (d, 1H).

b) 1-Bromo-2-(2-(methoxymethoxy)ethyl)benzene: Sodium hydride (60% dispersion in mineral oil, 0.966 g, 24.1 mmol) was placed in a 250 mL round bottom flask under N$_2$. The NaH was washed with dry hexanes (10 mL). The hexanes were removed via cannula, and the process repeated twice (2×10 mL). The NaH was dried under vacuum until a free flowing powder resulted and placed under N$_2$. 2-(2-bromophenyl)ethanol (4.016 g, 20 mmol) was dissolved in 60 mL of dry THF and added dropwise to the solid NaH. Once H$_2$ evolution had ceased, the solution was refluxed for 1 hour. The solution was allowed to cool to room temperature then cooled to 0° C. in an ice bath. Chloromethyl methyl ether (1.52 mL, 20 mmol) was then added and the solution allowed to warm to room temperature. The solution was stirred at room temperature for 18 hours then filtered through a 1.5 cm column of Celite. The Celite was washed with THF (2×15 mL). The THF filtrates were combined and evaporated under vacuum to give pure methoxymethoxy ether as an oil (4.64 g, 95%): $^1$H NMR δ 3.06 (t, 2H), 3.31 (s, 3H), 3.78 (t, 2H), 4.62 (s, 2H), 7.08 (dt, 1H), 7.26 (m, 2H), 7.54 (dd, 1H).

c) (3-Chlorophenyl)(2'-(2-(methoxymethoxy)ethyl)phenyl)borinic acid: 1-Bromo-2-(2-(methoxymethoxy)ethyl)benzene (2.21 g, 9.0 mmol) was dissolved in 50 mL of dry THF under N$_2$ and cooled to −78° C. t-BuLi (1.7M in pentane) (11.7 mL, 19.9 mmol) was slowly added to the solution. After stirring for 15 minutes at −78° C., 2-(3-chlorophenyl)-[1,3,2]dioxaborolane in 10 mL of dry THF was added and the solution stirred for a further 0.5 hours. The solution was then allowed to warm to room temperature and stirred for 18 hours. The THF was removed under vacuum and the residue partitioned between 50 mL of H$_2$O and 80 mL of diethyl ether. The solution was vigorously stirred for several minutes then neutralized (pH=7) with 6N HCl. The ether was separated and the aqueous solution extracted again with ether (2×50 mL). The ether extracts were combined, dried with MgSO$_4$, filtered and evaporated to give an orange oil (2.83 g). $^1$H NMR of the product showed that the desired borinic acid was formed. This was used for the next step without purification.

d) 1-(3-Chlorophenyl)-3,4-dihydro-1H-benzo[c][1,2]oxaborinine: The crude MOM protected borinic acid (2.83 g) was dissolved in 46 mL of THF and 4 mL of concentrated HCl. The solution was stirred at room temperature for 12 hours. 10 mL of H$_2$O was then added and the THF removed under vacuum. The aqueous solution was extracted with diethyl ether (3×50 mL). The ether extracts were combined and washed with brine until neutral. The ether was dried with MgSO$_4$, filtered and evaporated to give an orange oil (2.5 g). The crude product was purified by column chromatography on silica gel using 5:1 hexanes:ethyl acetate as eluent. After removal of the solvents, pure product (Rf=0.66) was obtained as a yellow oil (0.600 g, 27%; two steps): $^1$H NMR δ 3.03 (t, 2H), 4.35 (t, 2H), 7.26 (d, 1H), 7.32-7.39 (2H), 7.44-7.50 (2H), 7.75 (d, 1H), 7.79 (d, 1H), 7.85 (m, 1H): MS (ES$^-$) 243.01; HPLC [ret. time (% area)] 14.623 min (96.8%).

What is claimed is:
1. A compound having the structure of Formula 1

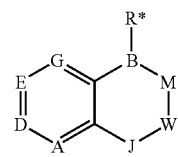

Formula 1 wherein B is boron, M is oxygen wherein R* is substituted or unsubstituted aryl, and wherein A is CH or CR$^1$ and wherein D is CR$^2$ and wherein E is CH or CR$^3$ and wherein G is CH or CR$^4$ and wherein J is (CH$_2$)$_n$ (n=1)

and wherein W is (CH$_2$)$_m$ (m=0)

wherein R$^2$ is a member selected from the group consisting of haloalkyl, alkyl, (CH$_2$)$_p$OH (p=1 to 3), halogen, CHO, CH=NOH, CO$_2$H, CO$_2$-alkyl, S-alkyl, SO$_2$-alkyl, S-aryl, (CH$_2$)$_q$NR$^{18}$R$^{19}$ (wherein R$^{18}$ and R$^{19}$ are independently selected from hydrogen, alkyl, and alkanoyl) (q=0 to 2), alkoxy, CF$_3$, SCF$_3$, NO$_2$, SO$_3$H, OH, substituted or unsubstituted aryl, substituted or unsubstituted aralkyl, substituted or unsubstituted heteroaryl, fused substituted or unsubstituted aryl, fused substituted or unsubstituted heteroaryl, R$^1$, R$^3$ and R$^4$ are each independently selected from the group consisting of hydrogen, haloalkyl, alkyl, (CH$_2$)$_p$OH (p=1 to 3), halogen, CHO, CH=NOH, CO$_2$H, CO$_2$-alkyl, S-alkyl, SO$_2$-alkyl, S-aryl, (CH$_2$)$_q$NR$^{18}$R$^{19}$ (wherein R$^{18}$ and R$^{19}$ are independently selected from hydrogen, alkyl, and alkanoyl) (q=0 to 2), alkoxy, CF$_3$, SCF$_3$, NO$_2$, SO$_3$H, OH, substituted or unsubstituted aryl, substituted or unsubstituted aralkyl, substituted or unsubstituted heteroaryl, fused substituted or unsubstituted aryl, fused substituted or unsubstituted heteroaryl, or a salt thereof including pharmaceutically acceptable salts.

2. The compound of claim 1 wherein R* has the structure

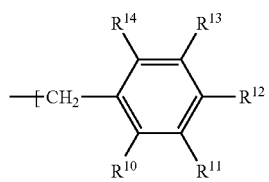

wherein R$^{10}$, R$^{11}$, R$^{12}$, R$^{13}$ and R$^{14}$ are each independently selected from the group consisting of hydrogen, alkyl, aryl, substituted aryl, aralkyl, substituted aralkyl, (CH$_2$)$_s$OH (where s=1 to 3), CO$_2$H, CO$_2$alkyl, CONH$_2$, CON-Halkyl, CON(alkyl)$_2$, OH, alkoxy, aryloxy, SH, S-alkyl, S-aryl, SO$_2$alkyl, SO$_3$H, SCF$_3$, CN, halogen, CF$_3$, NO$_2$, (CH$_2$)$_t$NR$^{22}$R$^{23}$ (wherein R$^{22}$ and R$^{23}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

3. A composition comprising a compound of claim 1 in a pharmaceutically acceptable carrier.

4. A method for inhibiting bacterial growth comprising contacting a bacterium with a compound of claim 1.

5. The method of claim 4 wherein R* has the structure

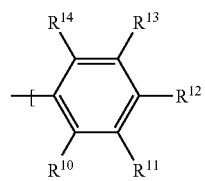

wherein R$^{10}$, R$^{11}$, R$^{12}$, R$^{13}$ and R$^{14}$ are each independently selected from the group consisting of hydrogen, alkyl, aryl, substituted aryl, aralkyl, substituted aralkyl, (CH$_2$)$_s$OH (where s=1 to 3), CO$_2$H, CO$_2$alkyl, CONH$_2$, CON-Halkyl, CON(alkyl)$_2$, OH, alkoxy, aryloxy, SH, S-alkyl, S-aryl, SO$_2$alkyl, SO$_3$H, SCF$_3$, CN, halogen, CF$_3$, NO$_2$, (CH$_2$)$_t$NR$^{22}$R$^{23}$ (wherein R$^{22}$ and R$^{22}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

6. The method of claim 4 wherein said compound has a structure which is a member selected from

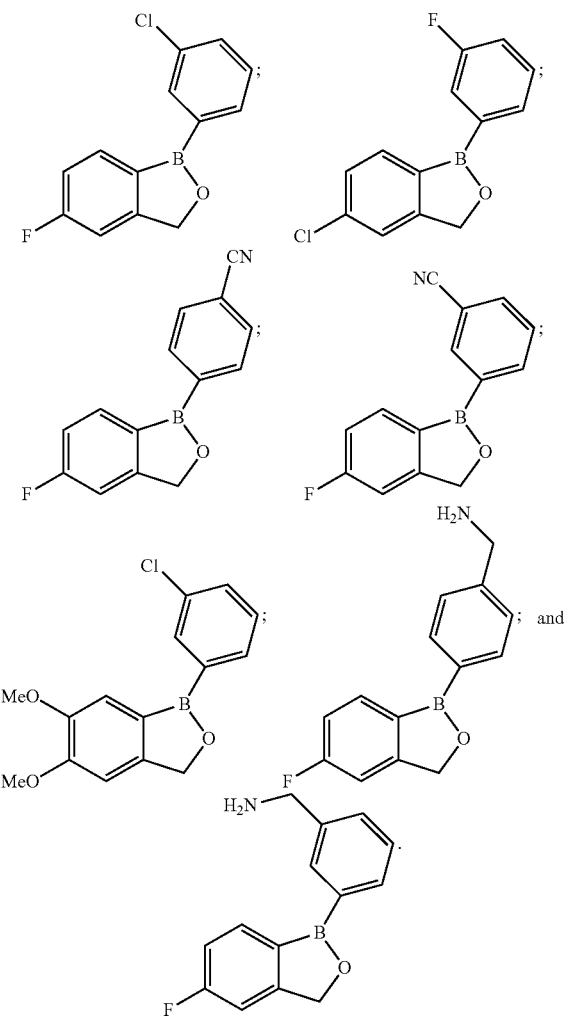

7. The method of claim 4 wherein said contacting occurs in vivo.

8. A method for inhibiting viral multiplication comprising contacting a virus with a compound of claim 1; wherein the virus is selected from a group consisting of Yellow Fever and Hepatitis.

9. The method of claim 8 wherein R* has the structure

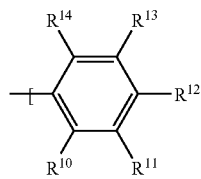

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$OH (where s=1 to 3), $CO_2H$, $CO_2$alkyl, $CONH_2$, CON-Halkyl, CON(alkyl)$_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{22}R^{23}$ (wherein $R^{22}$ and $R^{23}$ are independently selected from hydrogen, alkyl, and alkanoyl) (t=0 to 2), $SO_2NH_2$, $OCH_2CH_2NH_2$, $OCH_2CH_2NH$alkyl, $OCH_2CH_2N$(alkyl)$_2$, oxazolidin-2-yl, or alkyl substituted oxazolidin-2-yl.

10. The method of claim 8 wherein said compound has a structure which is a member selected from

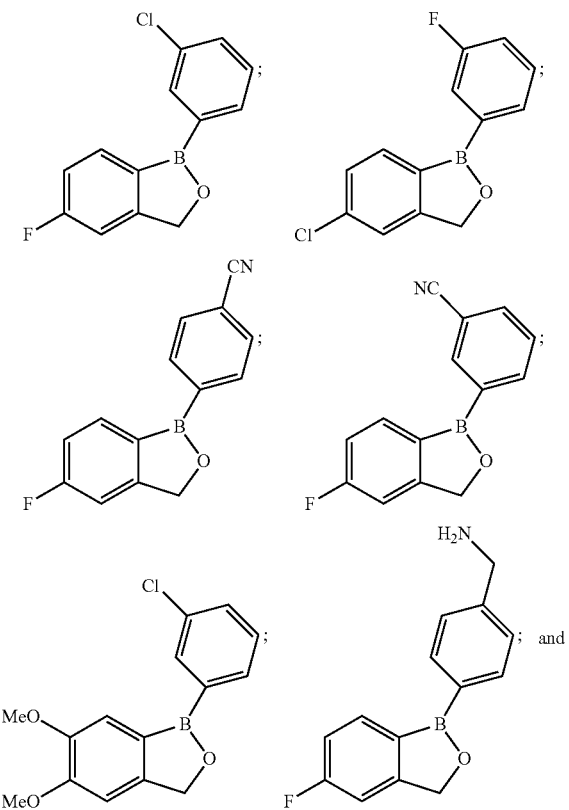

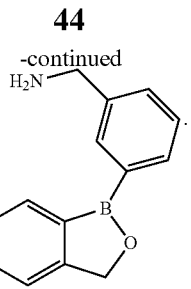

11. The method of claim 8 wherein said contacting occurs in vivo.

12. A compound having the structure of Formula 1

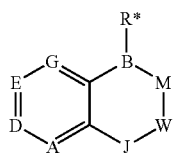

Formula 1 wherein B is boron, M is oxygen,
wherein R* is substituted or unsubstituted aryl,
and wherein A is $CR^1$
and wherein D is CH or $CR^2$
and wherein E is CH or $CR^3$
and wherein G is CH or $CR^4$
and wherein J is $(CH_2)_n$ (n=1) and wherein W is $(CH_2)_m$ (m=0)
wherein $R^1$ is a member selected from the group consisting of haloalkyl, alkyl, $(CH_2)_pOH$ (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl)(q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl, $R^2$, $R^3$ and $R^4$ are each independently selected from the group consisting of hydrogen, haloalkyl, alkyl, $(CH_2)_pOH$ (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl)(q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl, or a salt thereof including pharmaceutically acceptable salts.

13. The compound of claim 12 wherein R* has the structure:

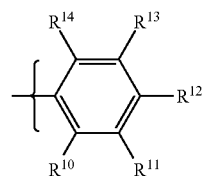

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$ OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{22}R^{23}$ (wherein $R^{22}$ and $R^{23}$ are independently selected from hydrogen, alkyl, and alkanoyl) (t=0 to 2), $SO_2NH_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

14. A compound having the structure of Formula 1

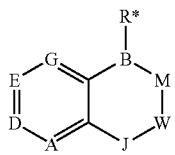

Formula 1 wherein B is boron, M is oxygen,
wherein R* is substituted or unsubstituted aryl,
and wherein A is CH or $CR^1$
and wherein D is CH or $CR^2$
and wherein E is $CR^3$
and wherein G is CH or $CR^4$
and wherein J is $(CH_2)_n$ (n=1)
and wherein W is $(CH_2)_m$ (m=0)
wherein $R^3$ is a member selected from the group consisting of haloalkyl, alkyl, $(CH_2)_pOH$ (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl)(q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl
$R^1$, $R^2$ and $R^4$ are each independently selected from the group consisting of hydrogen, haloalkyl, alkyl, $(CH_2)_p$ OH (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl)(q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl, or a salt thereof including pharmaceutically acceptable salts.

15. The compound of claim 14 wherein R* has the structure:

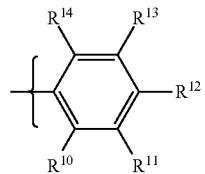

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$ OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{22}R^{23}$ (wherein $R^{22}$ and $R^{23}$ are independently selected from hydrogen, alkyl, and alkanoyl) (t=0 to 2), $SO_2NH_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

16. A compound having the structure of Formula 1

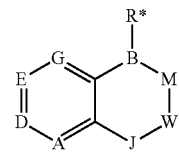

Formula 1 wherein B is boron, M is oxygen,
wherein R* is substituted or unsubstituted aryl,
and wherein A is CH or $CR^1$
and wherein D is CH or $CR^2$
and wherein E is CH or $CR^3$
and wherein G is $CR^4$
and wherein J is $(CH_2)_n$ (n=1)
and wherein W is $(CH_2)_m$ (m=0)
wherein $R^4$ is a member selected from the group consisting of haloalkyl, alkyl, $(CH_2)_pOH$ (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl) (q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl
$R^1$, $R^2$ and $R^3$ are each independently selected from the group consisting of hydrogen, haloalkyl, alkyl, $(CH_2)_p$ OH (p=1 to 3), halogen, CHO, CH=NOH, $CO_2H$, $CO_2$-alkyl, S-alkyl, $SO_2$-alkyl, S-aryl, $(CH_2)_qNR^{18}R^{19}$ (wherein $R^{18}$ and $R^{19}$ are independently selected from hydrogen, alkyl, and alkanoyl) (q=0 to 2), alkoxy, $CF_3$, $SCF_3$, $NO_2$, $SO_3H$, OH, substituted or unsubstituted aryl, substituted or unsubstituted aralkyl, substituted or unsubstituted heteroaryl, fused substituted or unsubstituted aryl, fused substituted or unsubstituted heteroaryl, or a salt thereof including pharmaceutically acceptable salts.

17. The compound of claim 16 wherein R* has the structure:

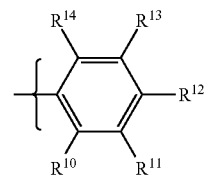

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$ OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{22}R^{23}$ (wherein $R^{22}$ and $R^{23}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

18. The compound of claim 1 wherein R$^2$ is halogen or alkoxy; and R$^1$, R$^3$ and R$^4$ are each independently selected from the group consisting of hydrogen, halogen and alkoxy.

19. The compound of claim 2 wherein R$^{10}$, R$^{11}$, R$^{12}$, R$^{13}$ and R$^{14}$ are each independently selected from the group consisting of hydrogen, (CH$_2$)$_s$OH (where s=1), OH, alkoxy, aryloxy, CN, halogen, (CH$_2$)$_t$NR$^{22}$R$^{23}$ (wherein R$^{22}$ and R$^{23}$ are independently selected from hydrogen and alkyl) (t=1).

20. The compound of claim 12 wherein R$^1$ is halogen or alkoxy; and R$^2$, R$^3$ and R$^4$ are each independently selected from the group consisting of hydrogen, halogen and alkoxy.

21. The compound of claim 13 wherein R$^{10}$, R$^{11}$, R$^{12}$, R$^{13}$ and R$^{14}$ are each independently selected from the group consisting of hydrogen, (CH$_2$)$_s$OH (where s=1), OH, alkoxy, aryloxy, CN, halogen, (CH$_2$)NR$^{22}$R$^{23}$ (wherein R$^{22}$ and R$^{23}$ are independently selected from hydrogen and alkyl) (t=1).

22. A composition comprising a compound of claim 12 in a pharmaceutically acceptable carrier.

23. The compound of claim 14 wherein R$^3$ is halogen or alkoxy; and R$^1$, R$^2$ and R$^4$ are each independently selected from the group consisting of hydrogen, halogen and alkoxy.

24. The compound of claim 15 wherein R$^{10}$, R$^{11}$, R$^{12}$, R$^{13}$ and R$^{14}$ are each independently selected from the group consisting of hydrogen, (CH$_2$)$_s$OH (where s=1), OH, alkoxy, aryloxy, CN, halogen, (CH$_2$)$_t$NR$^{22}$R$^{23}$ (wherein R$^{22}$ and R$^{23}$ are independently selected from hydrogen and alkyl) (t=1).

25. A composition comprising a compound of claim 14 in a pharmaceutically acceptable carrier.

26. The compound of claim 16 wherein R$^4$ is halogen or alkoxy; and R$^1$, R$^2$ and R$^3$ are each independently selected from the group consisting of hydrogen, halogen and alkoxy.

27. The compound of claim 17 wherein R$^{10}$, R$^{11}$, R$^{12}$, R$^{13}$ and R$^{14}$ are each independently selected from the group consisting of hydrogen, (CH$_2$)$_s$OH (where s=1), OH, alkoxy, aryloxy, CN, halogen, (CH$_2$)$_t$NR$^{22}$R$^{23}$ (wherein R$^{22}$ and R$^{23}$ are independently selected from hydrogen and alkyl) (t=1).

28. A composition comprising a compound of claim 16 in a pharmaceutically acceptable carrier.

29. A method for inhibiting bacterial growth comprising contacting a bacterium with a compound of claim 12.

30. The method of claim 29 wherein R* has the structure

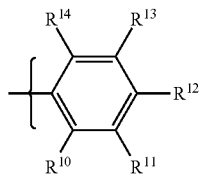

wherein R$^{10}$, R$^{11}$, R$^{12}$, R$^{13}$ and R$^{14}$ are each independently selected from the group consisting of hydrogen, alkyl, aryl, substituted aryl, aralkyl, substituted aralkyl, (CH$_2$)$_s$OH (where s=1 to 3), CO$_2$H, CO$_2$alkyl, CONH$_2$, CON-Halkyl, CON(alkyl)$_2$, OH, alkoxy, aryloxy, SH, S-alkyl, S-aryl, SO$_2$alkyl, SO$_3$H, SCF$_3$, CN, halogen, CF$_3$, NO$_2$, (CH$_2$)$_t$NR$^{22}$R$^{23}$ (wherein R$^{22}$ and R$^{22}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

31. The method of claim 29 wherein said contacting occurs in vivo.

32. A method for inhibiting viral multiplication comprising contacting a virus with a compound of claim 12; wherein the virus is selected from a group consisting of Yellow Fever and Hepatitis.

33. The method of claim 32 wherein R* has the structure

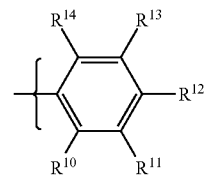

wherein R$^{10}$, R$^{11}$, R$^{12}$, R$^{13}$ and R$^{14}$ are each independently selected from the group consisting of hydrogen, alkyl, aryl, substituted aryl, aralkyl, substituted aralkyl, (CH$_2$)$_s$OH (where s=1 to 3), CO$_2$H, CO$_2$alkyl, CONH$_2$, CON-Halkyl, CON(alkyl)$_2$, OH, alkoxy, aryloxy, SH, S-alkyl, S-aryl, SO$_2$alkyl, SO$_3$H, SCF$_3$, CN, halogen, CF$_3$, NO$_2$, (CH$_2$)$_t$NR$^{22}$R$^{23}$ (wherein R$^{22}$ and R$^{23}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

34. The method of claim 32 wherein said contacting occurs in vivo.

35. A method for inhibiting bacterial growth comprising contacting a bacterium with a compound of claim 14.

36. The method of claim 35 wherein R* has the structure

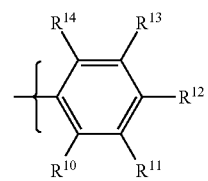

wherein R$^{10}$, R$^{11}$, R$^{12}$, R$^{13}$ and R$^{14}$ are each independently selected from the group consisting of hydrogen, alkyl, aryl, substituted aryl, aralkyl, substituted aralkyl, (CH$_2$)$_s$OH (where s=1 to 3), CO$_2$H, CO$_2$alkyl, CONH$_2$, CON-Halkyl, CON(alkyl)$_2$, OH, alkoxy, aryloxy, SH, S-alkyl, S-aryl, SO$_2$alkyl, SO$_3$H, SCF$_3$, CN, halogen, CF$_3$, NO$_2$, (CH$_2$)NR$^{22}$R$^{23}$ (wherein R$^{22}$ and R$^{22}$ are independently selected from hydrogen, alkyl, and alkanoyl) (t=0 to 2), SO$_2$NH$_2$, OCH$_2$CH$_2$NH$_2$, OCH$_2$CH$_2$NHalkyl, OCH$_2$CH$_2$N(alkyl)$_2$, oxazolidin-2-yl, or alkyl substituted oxazolidin-2-yl.

37. The method of claim 35 wherein said compound has a structure which is a member selected from

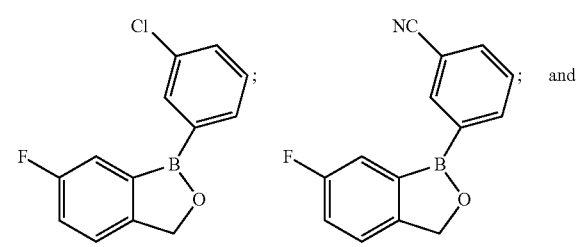

and

-continued

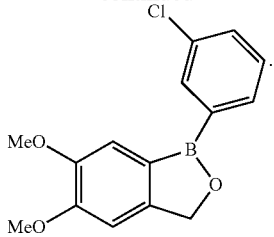

38. The method of claim 35 wherein said contacting occurs in vivo.

39. A method for inhibiting viral multiplication comprising contacting a virus with a compound of claim 14; wherein the virus is selected from a group consisting of Yellow Fever end Hepatitis.

40. The method of claim 39 wherein R* has the structure

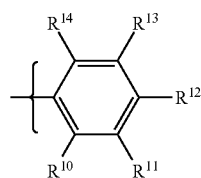

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{22}R^{23}$ (wherein $R^{22}$ and $R^{23}$ are independently selected from hydrogen, alkyl, and alkanoyl) (t=0 to 2), $SO_2NH_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

41. The method of claim 39 wherein said compound has a structure which is a member selected from

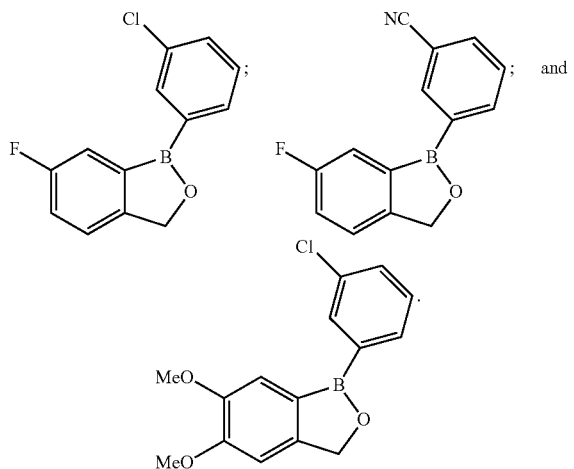

42. The method of claim 39 wherein said contacting occurs in vivo.

43. A method for inhibiting bacterial growth comprising contacting a bacterium with a compound of claim 16.

44. The method of claim 43 wherein R* has the structure

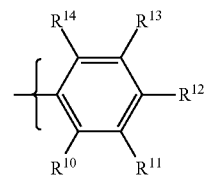

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)NR^{22}R^{23}$ (wherein $R^{22}$ and $R^{22}$ are independently selected from hydrogen, alkyl, and alkanoyl) (t=0 to 2), $SO_2NH_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

45. The method of claim 43 wherein said contacting occurs in vivo.

46. A method for inhibiting viral multiplication comprising contacting a virus with a compound of claim 16; wherein the virus is selected from a group consisting of Yellow Fever and Hepatitis.

47. The method of claim 46 wherein R* has the structure

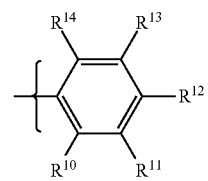

wherein $R^{10}$, $R^{11}$, $R^{12}$, $R^{13}$ and $R^{14}$ are each independently selected from the group consisting of hydrogen, alkyl, aryl, substituted aryl, aralkyl, substituted aralkyl, $(CH_2)_s$OH (where s=1 to 3), $CO_2H$, $CO_2$alkyl, $CONH_2$, CON-Halkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)NR^{22}R^{23}$ (wherein $R^{22}$ and $R^{23}$ are independently selected from hydrogen, alkyl, and alkanoyl) (t=0 to 2), $SO_2NH_2$, $OCH_2CH_2NH_2$, $OCH_2CH_2NHalkyl$, $OCH_2CH_2N(alkyl)_2$, oxazolidin-2-yl, or alkyl substituted oxazolidin-2-yl.

48. The method of claim 46 wherein said contacting occurs in vivo.

\* \* \* \* \*